United States Patent
Davis et al.

(10) Patent No.: US 11,821,034 B2
(45) Date of Patent: *Nov. 21, 2023

(54) NUCLEIC ACID SAMPLE PREPARATION METHODS

(71) Applicant: Roche Sequencing Solutions, Inc., Pleasanton, CA (US)

(72) Inventors: Randall Davis, Pleasanton, CA (US); Michael Dorwart, San Jose, CA (US); Janine Mok, Palo Alto, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/386,995

(22) Filed: Jul. 28, 2021

(65) Prior Publication Data

US 2022/0017959 A1 Jan. 20, 2022

Related U.S. Application Data

(63) Continuation of application No. 16/152,378, filed on Oct. 4, 2018, now Pat. No. 11,111,534, which is a continuation of application No. PCT/EP2017/057974, filed on Apr. 4, 2017.

(60) Provisional application No. 62/407,357, filed on Oct. 12, 2016, provisional application No. 62/318,187, filed on Apr. 4, 2016.

(51) Int. Cl.
| | |
|---|---|
| *C12Q 1/68* | (2018.01) |
| *C12Q 1/6874* | (2018.01) |
| *C12Q 1/6806* | (2018.01) |
| *C12Q 1/6869* | (2018.01) |
| *C07H 21/02* | (2006.01) |

(52) U.S. Cl.
CPC ......... *C12Q 1/6874* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 11,111,534 B2 * | 9/2021 | Davis et al. ......... | C12Q 1/6869 |
| 2017/0037459 A1 | 2/2017 | Godwin et al. | |
| 2018/0087108 A1 | 3/2018 | Berka et al. | |

FOREIGN PATENT DOCUMENTS

| | | |
|---|---|---|
| WO | 2007/087262 A2 | 8/2007 |
| WO | 2009/120372 A2 | 10/2009 |
| WO | 2012/103154 A1 | 8/2012 |
| WO | 2013/102091 A1 | 7/2013 |

OTHER PUBLICATIONS

International Bureau on behalf of the International Searching Authority, International Preliminary Report on Patentability, for International Patent Application No. PCT/EP2017/057974 (dated Oct. 9, 2018).
International Searching Authority, International Search Report, for International Patent Application No. PCT/EP2017/057974 (dated Oct. 12, 2017).
International Searching Authority, Written Opinion of the International Searching Authority, for International Patent Application No. PCT/EP2017/057974 (dated Oct. 12, 2017).

* cited by examiner

*Primary Examiner* — Bradley L. Sisson
(74) *Attorney, Agent, or Firm* — Eric Grant Lee

(57) ABSTRACT

Provided are methods of nucleic acid sample preparation for analysis, including analysis using nanopore sequencing applications. In particular provided are methods that allow for the creation of circular and linear DNA samples that contain asymmetric ends to ligate different and desired adaptors to the end of the sample, methods to create single nucleic acid molecules that automatically form concatemers for higher sequencing throughput; methods to create multiple copies (temperature dependent, multi-primed, openfold replication) of one original nucleic acid sample, or to create single nucleic acid molecules containing multiple copies of more than one original nucleic acid sample (concatemerized samples) for improved accuracy and throughput are described; and methods for improved modified base calling.

11 Claims, 23 Drawing Sheets

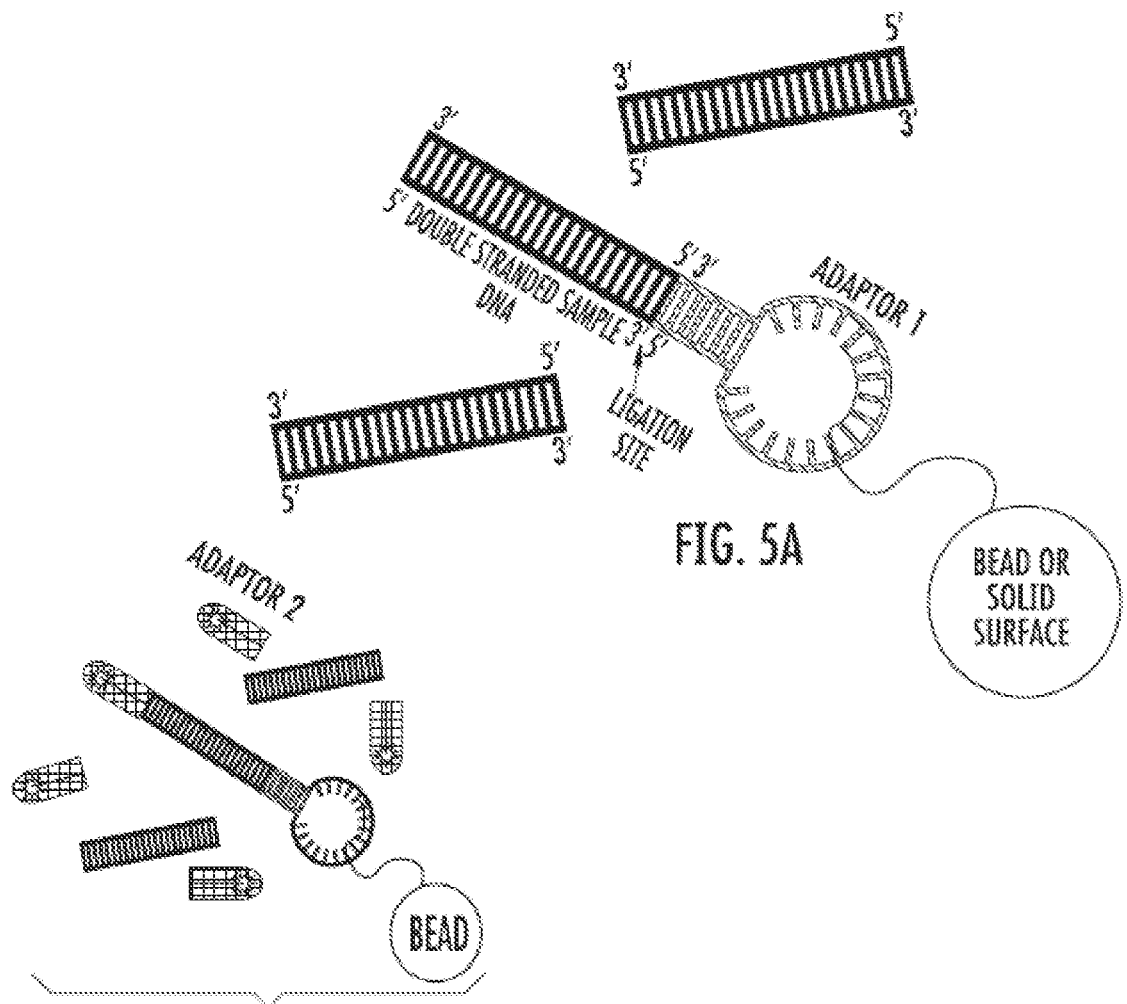
FIG. 5A
FIG. 5B
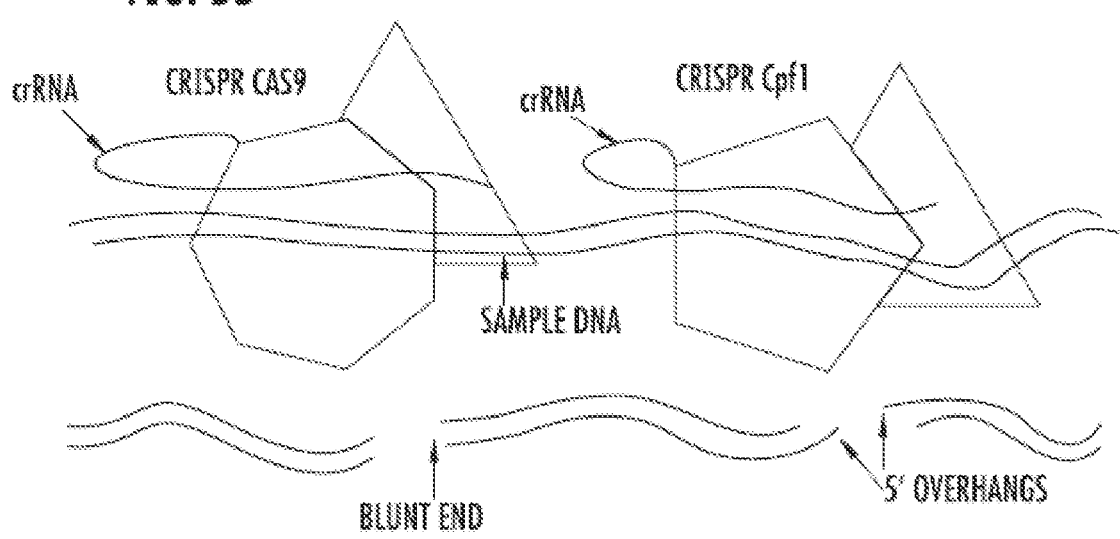
FIG. 6

NUCLEIC ACID SAMPLE PREPARATION METHODS

CROSS REFERENCE TO RELATED APPLICATIONS

This is a continuation application of U.S. patent application Ser. No. 16/152,378, filed Oct. 4, 2018, which, which is a continuation of International Patent Application No. PCT/EP2017/057974, filed Apr. 4, 2017, which claims priority from U.S. Provisional Patent Application No. US 62/318,187, filed Apr. 4, 2016, and claims priority from U.S. Provisional Patent Application No. 62/407,357, filed Oct. 12, 2016.

FIELD OF THE INVENTION

The present invention provides methods of nucleic acid sample preparation for analysis, including sequence analysis using biological or non-biological nanopores.

BACKGROUND OF THE INVENTION

DNA Sequencing using an array of nanopores is a promising method to create single molecule, low cost, high speed, and highly accurate sequence information from a strand of DNA or RNA. Methods to determine the sequence of a nucleic acid polymer using nanopores include strand sequencing, optical detection, and nanotag sequencing. Strand sequencing electrophoretically pulls the DNA sample through a nanopore and detects fluctuations in signal across the nanopore as the base composition in the pore changes. Another method of single molecule sequencing uses optical detection to read the base-specific light emitted from fluorescently labeled nucleotides as they are incorporated into a newly synthesized strand during sequencing by synthesis. Nanotage sequencing is based on sequencing by synthesis and locates a polymerase bound to template DNA at the top of a nanopore. As the polymerase incorporates nucleotides into the newly forming copy strand, each nucleotide contains a base-specific tag that is caught in the nanopore and gives a base specific signal.

Compiling the sequential reads from single molecule strand sequencing, optical sequencing, or nanotag sequencing allows one to construct the sequence of the sample. For single molecule sequencing methods, the sequencing accuracy is diminished because of the brief time that a signal representing a base is present in the detector, resulting from the stochastic nature of the DNA threading speed or DNA synthesis speed. To improve accuracy, the sample DNA is often read multiple times at the same sensor, and consensus reads are compiled for each sample fragment. In addition, all methods can benefit from the efficient loading and added throughput of reading multiple DNA samples at each sensor. For example, Circular Consensus Sequencing (CCS) allows for repeated reads of individual templates from a sample (Travers K. J., et al., A flexible and efficient template format for circular consensus sequencing and SNP detection. *Nucleic Acids Res.* 2010 August; 38(15):e159, Epub 2010 Jun. 22). Sample preparation plays an important role in allowing for replicate reads (Tsavachidou, Genomic DNA preparation enabling multiple replicate reads for accurate nanopore sequencing. bioRxiv preprint first posted online Dec. 28, 2015, dx.doi.org/10.1101/035436). There remains a need for novel sample preparation methods that result in higher accuracy and higher sample throughput for next generation single molecule sequencing.

BRIEF DESCRIPTION OF THE DRAWINGS

FIGS. 5A and 5B depict the construction of asymmetric ends on sample molecules using steric hindrance.

FIG. 6 depicts a programmable endonuclease mediated asymmetric sample preparation method.

FIG. 14A depicts the resulting linear molecule after one cycle of open-fold replication. FIG. 14B illustrates the results of additional cycles of concatemerization and openfold replication (using extension and ligation) resulting from the use of multiple primer sites and repeated ligation of hairpin sealed DNA fragments. FIG. 14C depicts an alternative (to the hairpin sealing adaptor) sealing component which further comprises at least one (or two) additional sample fragments. The cycle of primer extension and ligation of new hairpin-sealed sample fragments occurs in step-wise fashion.

FIGS. 15A-15I depict a strategy for using a multi-primer adaptor site at one end of a sample nucleic acid molecule while having a sealed adaptor at the other end of the molecule.

DEFINITIONS

Figure 1:
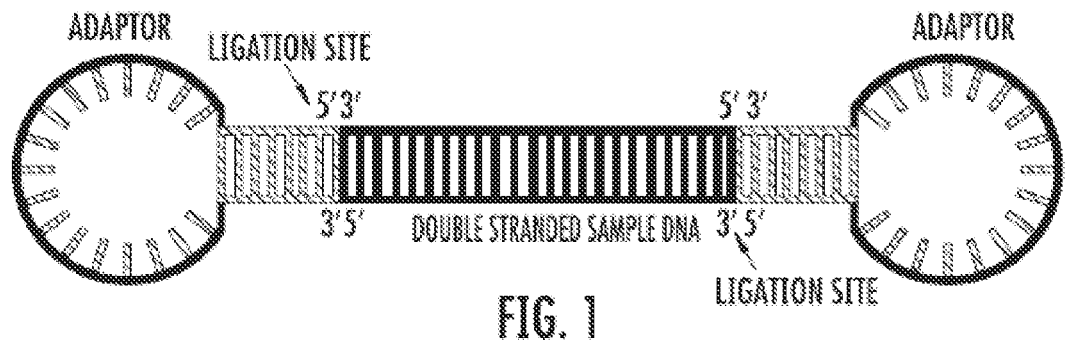
FIG. 1 depicts non-directional adaptor ligation for sequencing applications.

Unless defined otherwise, all technical and scientific terms used herein have the same meaning as commonly understood by one of ordinary skill in the art to which this invention pertains. Although essentially any methods and materials similar to those described herein can be used in the practice or testing of the present invention, only exemplary methods and materials are described. For purposes of the present invention, the following terms are defined below.

The terms "a," "an," and "the" include plural referents, unless the context clearly indicates otherwise.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from about six to about 175 nucleic acid monomer units, more typically from about eight to about 100 nucleic acid monomer units, and still more typically from about 10 to about 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. (*J. Am. Chem. Soc.* 103:3185-3191, 1981); automated synthesis methods; or the solid support method of Caruthers et al. U.S. Pat. No. 4,458,066, or other methods known to those skilled in the art. All of these references are incorporated by reference.

The term "primer" as used herein refers to a polynucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction)). To further illustrate, primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 40 nucleotides, more typically from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur. In certain embodiments, the term "primer pair" means a set of primers including a 5' sense primer (sometimes called "forward") that hybridizes with the complement of the 5' end of the nucleic acid sequence to be amplified and a 3' antisense primer (sometimes called "reverse") that hybridizes with the 3' end of the sequence to be amplified (e.g., if the target sequence is expressed as RNA or is an RNA). A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available.

The term "open-fold replication" or "open-fold extension" as used herein refers to a strategy for nucleic acid replication based upon a template nucleic acid molecule that comprises a double stranded duplex region, an open end for initiation of replication, and a closed end. In one embodiment, the double stranded duplex region comprises a sense strand and an antisense strand that are complementary. In another embodiment, the open end for initiation of replication includes an overhang region that comprises at least one primer site. In a preferred embodiment, the overhang region comprises a multi-priming site region. In another embodiment, the template nucleic acid molecule is a non-circular nucleic acid molecule. In other embodiments, the template nucleic acid molecule is a stem-loop nucleic acid molecule. In one other embodiment, the stem-loop molecule comprises a single stranded nucleic acid that engages in intramolecular base pairing. In one other embodiment, the closed end comprises a hairpin loop at one end of the stem-loop, wherein the hairpin loop comprises a nucleotide sequence that does not engage in intramolecular base pairing. As used herein, "open-fold replication" comprises the step of extending a nucleic acid that can adopt a linearized format. For example, a stem-loop nucleic acid molecule has an open end from which extension or replication can begin. As the extension reaction proceeds, the stem-loop structure gives way to a linearized structure.

The term "multi-priming", "multiple primer", or "multi-primer" site region as used herein refers to a nucleotide sequence comprising at least one and preferably two primer sites adjacent to one another. The multi-priming site region is generally engineered through the use of a suitable adaptor as described here at one end of a sample fragment.

The term "concatemer" or "concatemeric" as used herein refers to a single nucleic acid molecule containing at least two fragments from a sample that will be subjected to nucleic acid sequencing. The at least two fragments may be the same fragment or may be different fragments. Each fragment in the concatemer is separated from the other by a predetermined sequence. For example, the nucleic acid adapters described herein for providing asymmetric ends (or linking sequences joining two different sample nucleic acid molecules) are designed with a predetermined sequence. In the context of nucleic acid sequencing, the predetermined sequence permits the identification of the end of the sequence of one fragment and the beginning of the sequence of another fragment. In one embodiment, the concatemer molecules are linear nucleic acid molecules or circular nucleic acid molecules.

DETAILED DESCRIPTION OF THE INVENTION

The present invention provides methods of nucleic acid sample preparation for analysis, including analysis using nanopore sequencing applications. In one aspect, the described methods allow for the creation of circular and linear DNA samples that contain asymmetric ends to ligate different and desired adaptors to the end of the sample. Following from this, methods to create single nucleic acid molecules that automatically form concatemers for higher sequencing throughput are described. In addition, methods to create multiple copies (temperature dependent, multi-primed, open-fold replication) of one original nucleic acid sample, or to create single nucleic acid molecules containing multiple copies of more than one original nucleic acid sample (concatemerized samples) for improved accuracy and throughput are described. This is highly advantageous for estimating the run time needed to complete sequencing of concatemerized samples. Also, the creation of multiple copies of nucleic acid sample fragments in one nucleic acid molecule allows for improved modified base calling and this is herein described.

I. Nucleic Acid Molecules With Engineered Asymmetric Ends

The present invention provides methods of creating or engineering asymmetric ends on sample nucleic acid fragment(s) that can then be used create sample nucleic acid molecules with distinct advantages (e.g., such as for nanopore sequencing). These methods may be applied individually or combined as part of larger more complex methods and protocols. A common and accepted method for single molecule DNA sample preparation employs blunt end or single nucleotide tailing (e.g., single A tailing) of a single nucleic acid fragment from a sample to attach identical blunt end or corresponding single nucleotide (e.g., at single T nucleotide) overhang adaptors to both ends of double stranded DNA (FIG. 1).

FIG. 1 depicts the ligation of two identical adaptors onto the ends of a blunt ended or 3' tailed double stranded DNA fragment. The sample DNA is not modified, but this method provides nucleic acid molecules that have distinct limitations in nanopore sequencing, including, without limitation, that the molecule of FIG. 1 has two potential identical primer sites on one molecule, while only a single sample fragment is read, and the single sample fragment cannot be pulled through a nanopore to read bases because of its circular format. In addition, and unlike the present invention, the approach exemplified in FIG. 1 (i) does not lend itself to constructing concatemers to read multiple samples in a single nanopore sequencing run (e.g., at one sensor), and (ii) does not provide position by position comparisons of original (non-amplified) sample and constructed sample copies within the single nucleic acid sample to help in modified base determination.

By contrast, the present invention provides concatemer molecule creation methods that allow for the generation of a single nucleic acid molecule containing copies of sample fragments. The sample fragment will generally comprise both a sense and an antisense nucleic acid strand. In one embodiment, the methods allow for the creation of single nucleic acid concatemer molecules that contain (i) multiple copies of a single sample fragment, (ii) at least two distinct sample fragments, or (iii) multiple copies of more than one distinct sample fragment representing different regions of the same sample. In addition, the present invention provides methods that allow for the "step-wise", controlled attachment or ligation of multiple distinct sample fragments (i.e., formation of concatemers or concatemerization), and the subsequent creation of copies of these ligated fragments in a manner that preserves the single nucleic acid format. An important precursor to the use of the methods disclosed herein for concatemer formation is the selection and application of suitable asymmetric end adaptors to a plurality of sample fragments.

In one aspect, the methods allow for the creation of asymmetric ends on double stranded and single stranded nucleic acid fragments including, without limitation, (A) unidirectional extension methods, (B) steric hindrance methods, and (C) programmable endonuclease methods. In one embodiment, asymmetric ends can be created on genomic nucleic acid (e.g., genomic DNA or gDNA) or on an amplified population of double stranded nucleic acid (e.g., amplicons).

A. Unidirectional Extension

In one aspect, the present invention provides a method for creating asymmetric ends on double stranded and single stranded nucleic acid fragments using unidirectional extension. One method of creating asymmetric ends on unknown nucleic acid sample (e.g., DNA or RNA) is to create single stranded nucleic acid (e.g., DNA or RNA) and use an original nucleic acid primer to prime the 3' end of this single stranded sample and perform just one cycle of extension from the original primer. In one embodiment, the extension is performed by an enzyme that will attach a single untemplated nucleotide at the final base position of the newly extended strand. In a preferred embodiment, the extension is performed by an enzyme that will attach a single untemplated "A" at the final base position of the newly extended strand.

In another embodiment, the extension reaction is performed using tailing, which is an enzymatic method for adding a non-templated nucleotide to the 3' end of a blunt double stranded nucleic acid molecule. In the present invention, tailing is done to prepare an extended fragment from a sample for ligation to another extended fragment. For example, an extension reaction using Taq polymerase, or Klenow fragment (3'→5' exo-), will provide a single A (adenosine) extension at the 3' end of the extended double stranded fragment that will be complementary to a single T (thymidine) in an adaptor, as described herein. Tailing provides the advantage of not requiring the use of restriction endonucleases prior to ligation. In addition, primers need not be designed with restriction sites. In another preferred embodiment, the extension enzyme is Taq polymerase or Klenow polymerase. The creation of overhangs of various forms on the original primer allows the format of a single stranded sample to be changed to the format of a double stranded molecule with each end having a unique format of base overhangs. The hybridization site on the original primer may also be varied to accomplish priming of single stranded samples in variety of ways. In some embodiments, the priming method is selected from the group consisting of (i) site specific priming of the end of a known sample, (ii) all universal 3' base or partial universal base primer sequences with 5' hairpin overhangs that can ligated to the prime 3' sample ends, and (iii) random primers with 5' overhangs that can be used to create new full extension products on a single stranded genomic or amplicon DNA sample. In another embodiment, the unidirectional extension reaction is optionally required to create a single untemplated "A" on the 3' end of the newly extended strand. This is referred to as "tailing", which is an enzymatic method for adding a non-templated "A" nucleotide to the 3' end of a blunt double stranded nucleic acid molecule. In the present invention, tailing is done to prepare an extended fragment from a sample for ligation to an adaptor or another extended fragment. For example, an extension reaction using Taq polymerase, or Klenow fragment (3'→5' exo minus), will provide a single A (adenosine) extension at the 3' end of the extended double stranded fragment that will be complementary to a single T (thymidine) in an adaptor, as described herein. Tailing provides the advantage of making the tailed end more selective for the addition of molecules to its end. Only "T" overhang dsDNA adaptors or "T" overhang dsDNA will readily ligate to this end, making it unlikely that random DNA will ligate to the end.

In one additional embodiment, the unidirectional extension reaction is performed using a hairpin adapter/primer molecule which comprises a universal base region for priming to the single stranded sample nucleic acid and a double stranded duplex region that comprises a hairpin region. For example, a universal base region may be used to extend fragments from a genomic nucleic acid population obtained from a sample. Universal bases are analog compounds that can replace any of the four DNA bases without destabilizing base-pair interactions and therefore can pair with any of the four natural nucleotides. Alternatively, the extension reaction primer comprises a double stranded duplex region with a hairpin region and a known sequence region (instead of a universal base region) that is complementary to a 3' region of a nucleic acid population to be extended. In one embodiment, the nucleic acid population comprises amplicons from a prior amplification reaction using a designed primer pair(s).

Figure 2A:
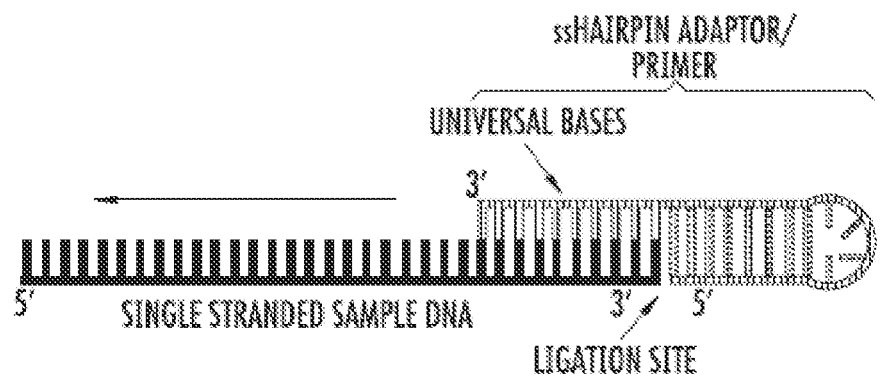
FIGS. 2A, 2B and 2C depict a method to create asymetric ends on sample nucleic acid using one time, unidirectional extension of a hairpin adaptor.
Figure 2B:
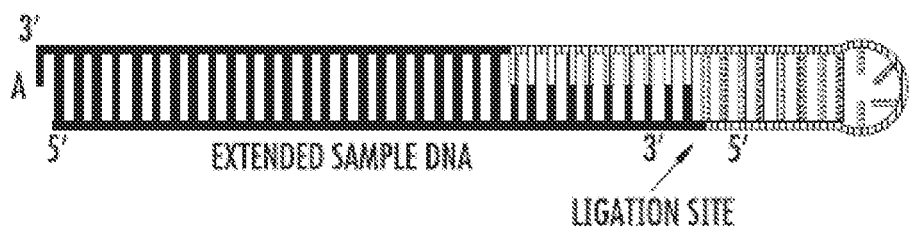
Figure 2C:
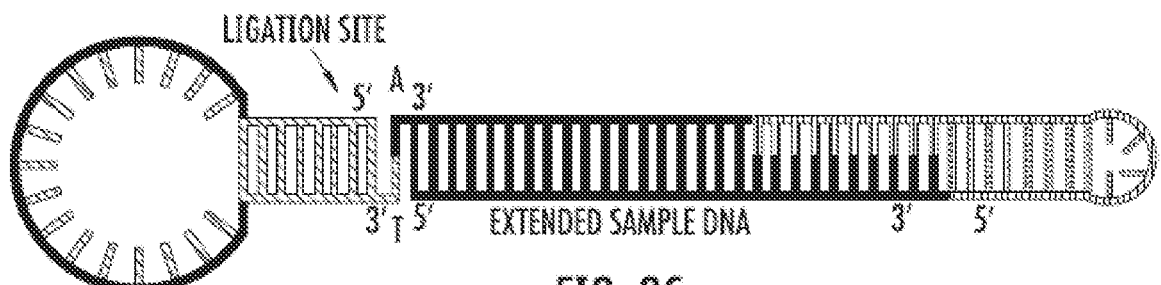

FIGS. 2A-C provide an example of a unidirectional extension method. FIG. 2A A universal hairpin molecule is used to prime and seal the 3' end of a single stranded DNA or RNA after a subsequent ligation step. FIG. 2B After extension by Klenow or Taq polymerase, a single 3' A overhang is provided on the open end of all loop fragments. FIG. 2C A different adaptor can be annealed to the A overhang and then ligated at the ligation site.

In one additional embodiment, the unidirectional extension reaction is performed using a primer containing a random base region at one end for priming to the single stranded sample nucleic acid and a unique sequence at the other end. In another embodiment, the random base region comprises a random primer from a random primer mixture and the unique sequence is formatted to be a nucleic acid 5' overhang region that does not interact with the sample nucleic acid. A random primer mixture is made up of short segments of single-stranded DNA (ssDNA) oligonucleotides that can be but are not limited to 6 nucleotides long (hexamers) and include every possible combination of bases (e.g., $4^6$=4,096 different combinations) in the mixture. The presence of all possible hexamers allows the primers to bind to any section of nucleic acid.

The unique sequence of the primer described above is not complementary to the single stranded sample nucleic acid. In another embodiment, the unique sequence may be any predetermined nucleic acid sequence including, without limitation, DNA, RNA, and universal pyrimidines, universal purines, or other non-natural or man-made nucleotide analogs. Alternatively, the extension primer comprises a unique sequence and a universal base region (instead of a random base region) for priming to the single stranded sample nucleic acid. In one other embodiment, the extension reaction comprises annealing a plurality of primers (e.g., universal or random) to the single stranded sample nucleic acid such that at least a first primer anneals at the 3'-most end of the strand. As a result, the extension of the first primer displaces any and all other random primers that have bound to the sample template including a second, third, fourth, fifth, etc. primer(s) that are displaced. After extension, the enzyme can be inactivated (e.g., via heat) and a digestion step may be performed. In one embodiment, the digestion step comprises adding an exonuclease (e.g., exonuclease I or exonuclease T) to digest all single stranded nucleic acid. In another embodiment, the extended population of extended fragments comprises a double stranded nucleic acid fragment having a first end and a second end. The first end comprises a single 3' A overhang and the second end comprises a unique sequence that is not complementary to the original single stranded sample template.

Figure 3A:
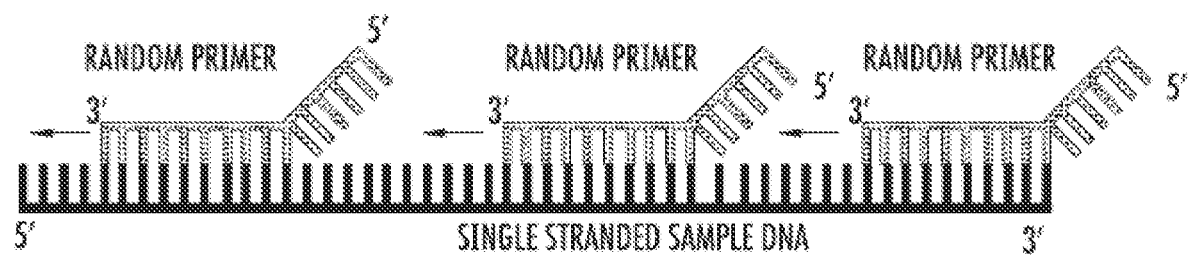
FIGS. 3A, 3B and 3C depict another method to create asymmetric ends on sample DNA using random or specific primers and one-time, unidirectional extension for genomic nucleic acid.
Figure 3B:
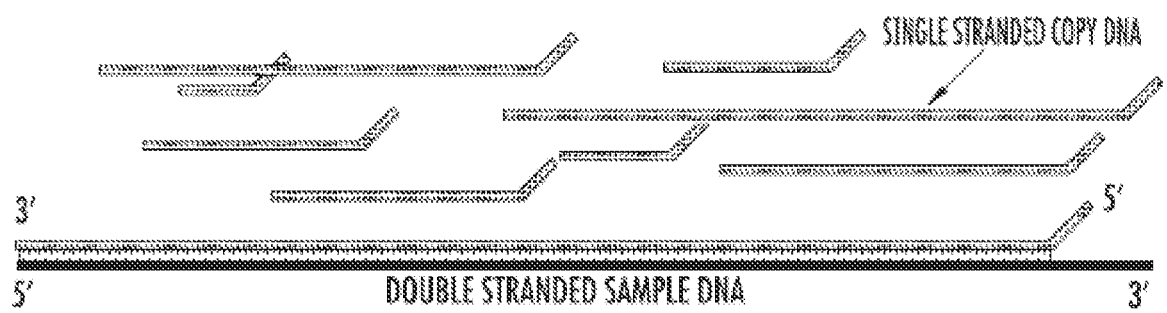
Figure 3C:

FIGS. 3A-C provide another example of a unidirectional extension method (e.g., unamplified genomic DNA or the last extension step for randomly amplified gDNA). FIG. 3A A single extension reaction is performed with 5' tailed random primers and Klenow 3'→5' exo minus enzyme. FIG. 3B Multiple primed sites will be extended on a single template DNA but the longest extended product starting from the most 3' of the original template will strand displace all (or most) shorter extension products. FIG. 3C After heat inactivation of the Klenow fragment, exonuclease T is added to the sample mix to digest all ssDNA from the 3' end and leaving dsDNA untouched. The result is a random primed double stranded DNA sample fragment with differentiated ends (i.e., a single 3' A overhang at one end (or after exo T treatment a blunt end on one end) and a unique sequence at the other 5' end) that can be used for further preparation (e.g., see FIGS. 4A-D).

In another aspect, the present invention provides a method comprising a unidirectional extension reaction combined with the ligation of one or more adaptors. As described herein, the extension reaction is performed using a primer containing a random base region (or universal base region) at one end for priming to the single stranded sample nucleic acid and a unique sequence at the other end. Alternatively, the extension reaction primer comprises a known nucleic acid sequence region (instead of a universal or random base region) that is complementary to a 3' region of a nucleic acid population (e.g., an amplicon population) to be extended at one end and a unique sequence at the other end.

In another embodiment, the method comprises the further step of ligating a first adaptor to the extended fragment at the site of the single A 3' overhang. In a preferred embodiment, the first adaptor comprises a double stranded nucleic acid molecule having a primer site region on one end or portion of the adaptor and a single T overhang on the other end of the adaptor. In another embodiment, the first adaptor is a double stranded (ds) nucleic acid molecule comprising a first strand having a primer binding region containing one or more primer sites (e.g., a multi-priming site region) at one end and a first complementary nucleic acid region for binding to the second strand at the other end, wherein the first complementary region further comprises an overhang. In a preferred embodiment, the overhang comprises (i) a single T 5' overhang for ligation to a corresponding single A 3' overhang, or (ii) a second complementary nucleic acid 5' overhang sequence for hybridization to a predetermined unique sequence that is created as part of a unidirectional extension reaction as described herein. In an additional embodiment, the first adaptor further comprises a second strand that comprises a nucleic acid sequence that is complementary to the first complementary nucleic acid region of the first strand.

In an additional embodiment, the method further comprises ligating a second adaptor at the site of the unique sequence provided by the extension primer. In a preferred embodiment, the second adaptor comprises a region that is complementary to the unique sequence at one end and a hairpin region at the other end.

Figure 4A:
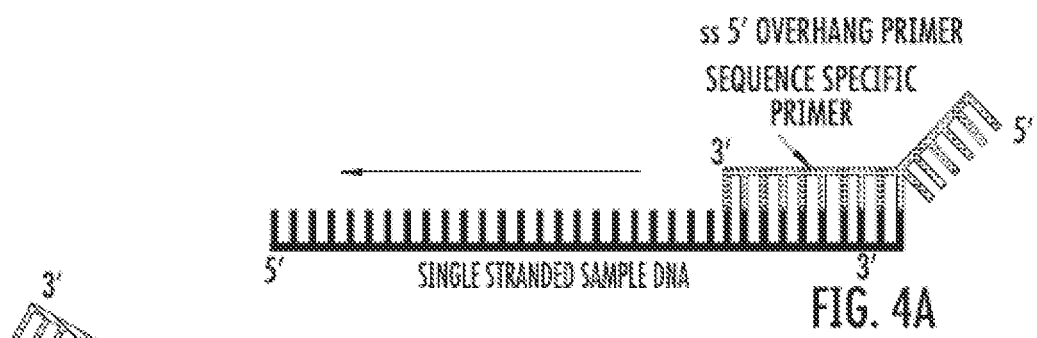
FIGS. 4A, 4B, 4C and 4D depict one additional unidirectional extension method creating asymetric ends that include single or multiple priming sites.
Figure 4B:
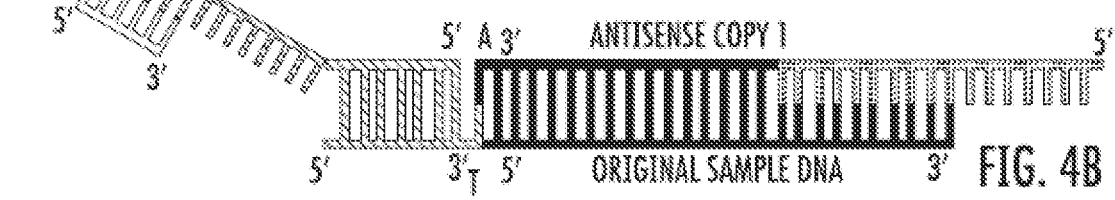
Figure 4C:
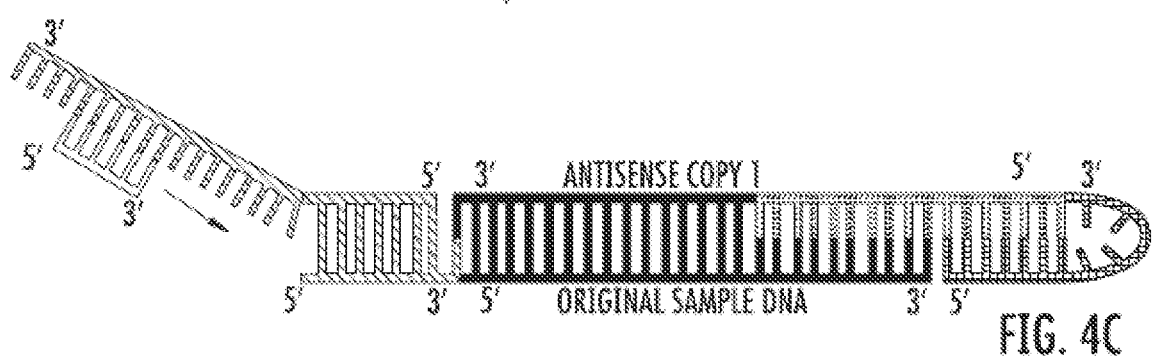
Figure 4D:
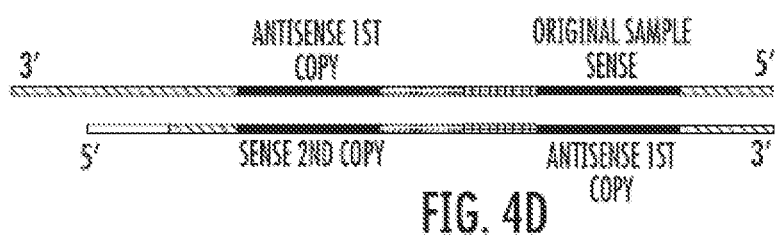

FIGS. 4A-D depict another unidirectional extension method with application for amplified DNA (e.g., amplicons), which is primed with specific primers at the last, single amplification cycle. FIG. 4A A single cycle of extension is performed using a first primer resulting in one end with a single 3' A overhang and one side with the primer end having a unique 5' overhang on the other side. FIG. 4B A "T" Tail Adaptor comprising a single 3' T overhang adaptor and a primer site region with at least 2 primer sites (e.g., multi-priming site region) is ligated to the differentiated double stranded (ds) DNA sample. FIG. 4C. An adaptor specific to the 5' overhang originating from said first primer is ligated to the other unique end, thereby forming a hairpin structure. FIG. 4D A primer hybridizing to an internal portion of said "T" Tail Adaptor serves as a starting point for an extension, such as an open-fold replication (as described herein). The primer may prime to a primer site that is part of a multi-priming site region. The resulting dsDNA molecule is shown in FIG. 4D and contains three copies of the original single stranded (ss) sample.

Alternatively, where the sequence of the template nucleic acid is known (e.g., amplified nucleic acid or amplicons), a hairpin adapter/primer molecule (which comprises a double stranded duplex region with a hairpin region and a known sequence region that is complementary to a 3' region of the amplicons to be extended) is used to specifically prime and extend, as well as seal the 3' end of the single stranded nucleic acid using a ligase step (e.g., FIG. 2A,B). For instance, the single stranded 5' overhang primer in FIG. 4A could be replaced with the hairpin molecule such that priming and sealing are provided in one step.

In one aspect, the present invention provides nucleic acid molecules (and methods of making the same) that are suitable for open-fold replication. Two important components for open-fold replication are exemplified in FIG. 4A-D. The ligation of a hairpin adaptor (FIG. 4C) to "seal" one end of a double stranded nucleic acid molecule allows it to "fold open" or linearize to a single stranded molecule. Upon linearization of the double stranded molecule (see FIG. 4D), the hybridization of a second primer in the multi-primer site (see FIG. 4B and FIGS. 15A-I and 16A-I) can be used to repeat replication of the linearized single stranded molecule.

B. Steric Hindrance

In one aspect, the present invention provides a method for creating asymmetric ends on double stranded and single stranded nucleic acid fragments using steric hindrance. FIGS. 5A-B depict an example of the construction of asymmetric ends on sample molecules using steric hindrance. FIG. 5A A suitable adaptor is bound to a solid surface (e.g., a bead) such that its movement is constricted. Free-floating adaptors are not present in the solution. DNA sample fragments are ligated to the adaptor and the probability that the other free end of the sample will hybridize with an adaptor on the same or other solid surface are lower than in free solution. FIG. 5B After an incubation time, the un-ligated sample is removed and a second adaptor is added to the bulk solution to ligate to the free end of the bound nucleic acid sample. Thus, different adaptors can be attached to opposite ends of the sample and an asymmetric molecule has been created.

In another aspect, the present invention provides a method for creating asymmetric ends based upon steric hindrance elements. In one embodiment, the method comprises blunt ending a plurality of nucleic acid fragments from a sample. In another embodiment, the method further comprises the step of providing a blunt end nucleic acid adaptor that is linked to a solid support. In one embodiment, the adaptor comprises a double stranded duplex region having a blunt end for ligation and a hairpin loop. In one other embodiment, the hairpin loop comprises a capture sequence site. The capture sequence site may be an enrichment site, which comprises a nucleic acid sequence that is complementary to a portion of the sequence of a capture oligonucleotide (see U.S. Provisional Patent App. No. 62/295,010 and International Patent Application No. PCT/EP2016/078781, which are incorporated herein by reference in their entireties). The capture oligonucleotide comprises a purification moiety at its 3' end and a sequence that is complementary to the loading capture site at its 5' end.

In another embodiment, the method further comprises contacting the plurality of blunt-ended fragments with the blunt end nucleic acid adaptor in the presence of a ligase to attach the fragments to the adaptors which are linked to the solid support. The term "solid support" or "solid support material" comprises any of the solid materials mentioned above in connection with the immobilization of nucleic acids, e.g., magnetic glass particles, glass fibers, glass fiber filters, filter paper etc., while the solid support material is not limited to these materials (see Eickhoff et al. U.S. Pat. No. 8,609,340, which is incorporated herein by reference in its entirety).

C. Programmable Endonuclease Methods

In one aspect, the present invention provides a method for creating asymmetric ends on double stranded and single stranded nucleic acid fragments using a programmable endonuclease method. In one embodiment, the present invention provides methods of creating a nucleic acid molecule with asymmetric ends for DNA sequencing in nanopores including programmable, site-specific enzymatic cleavage. The method uses the CRISPR Cas9 and CRISPR CpF1 proteins to cut double stranded sample DNA at sequences in a genome determined by independent guide RNA strands. Cas9 cuts in a blunt ended fashion and CpF1 cuts leaving overhangs, thus judicious selection of guide RNAs can create asymmetric ends (e.g., one end blunt and one end with an overhang strand) on processed sample DNA fragments for use in downstream sample preparation techniques.

FIG. 6 depicts a programmable endonuclease mediated asymmetric sample preparation method. CRISPR-CAS9 AND CRISPR-Cpf1 are RNA guided nucleases that match crRNA (Crispr RNA) sequences to dsDNA template and cut at matching sequences. CAS9 effector module protein creates blunt end cuts, Cpf1 effector module protein cuts dsDNA leaving 5-nucleotide-long 5' overhangs. By combining targeted ssRNA (crRNAs) with CRISPR CAS9 and separately or together combining different targeting RNAs with CRISPR Cpf1 like proteins, together or sequentially, patterned cuts resulting in sample fragments with one blunt end and one 5' overhang end can be created. The method can be used with or without amplified genomic nucleic acid. In addition, this method has the advantage of not requiring amplification of gDNA but still having the benefit of asymmetric sample processing.

D. Multi-Functional Nucleic Acid Molecules

The present invention provides methods of providing asymmetric ends to double stranded nucleic acid molecules such that the newly created ends provide additional functionality for the double stranded molecule. In one aspect, the functionality provided may be multi-functional in nature. For example, variety of multi-functional (e.g., bifunctional and trifunctional) nucleic acid templates may be prepared based upon the incorporation of functional elements through asymmetric end attachment. In one other embodiment, at least one of the adaptors comprises a functional element that adds one or more additional functionalities to the nucleic acid template that will be used for nanopore sequencing. In some embodiments, the functional element is a nucleic acid sequence. In other embodiments, the functional element is selected from the group consisting of a primer site, a capture sequence site, a calibration site, a barcode site for sample multiplexing, and any combination thereof. For example, at least one adaptor may comprise (i) a primer site for initiating sequencing or (ii) a capture sequence site.

In one embodiment, the methods comprise adding asymmetrical ends to sample nucleic acid to create a circular template or a non-circular template. In another embodiment, different adaptors are used to add the asymmetrical ends. For instance, a unidirectional extension reaction may be performed as described herein using tailing and an extension primer containing a random or universal base region (or alternatively a known nucleic acid sequence region that is complementary to a 3' region of a nucleic acid population, e.g., an amplicon population) at one end, while the other end of the extension primer comprises a unique nucleic acid sequence (see FIGS. 3A-C and 4A-D), thereby preparing the extended fragment for ligation to adaptors. In one embodiment, the method comprises ligating a first adaptor to the extended fragment at the site of the single A 3' overhang (e.g., see Adaptor 1 in FIG. 7). In a preferred embodiment, the first adaptor comprises a loop region with a single primer site and a double-stranded duplex region for ligation. In a further embodiment, the double stranded region comprises a single T overhang for ligation to the single A 3' overhang of the extended fragment. In an additional embodiment, the method further comprises ligating a second adaptor at the site of the unique sequence provided by the extension primer (e.g., see Adaptor 2 in FIG. 7). In a preferred embodiment, the second adaptor comprises a region that is complementary to the unique sequence (from the extension primer) at one end and a hairpin region at the other end.

Figure 7:
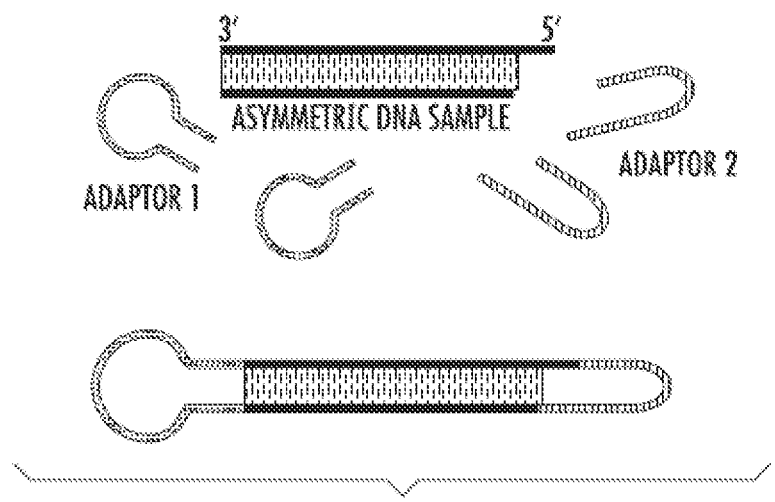
FIG. 7 depicts a strategy for creating a circular asymmetric DNA sample fragment with a single primer site.

FIG. 7 depicts a strategy for creating a circular asymmetric DNA sample fragment with a single primer site. Two adaptors each specific to one end will ligate to create a single primer site on a circular DNA sample. Adaptor 1 (FIG. 7, left side) may contain a primer site, an enrichment site, a calibration site, a barcode for sample multiplexing, or any combination thereof. Adaptor 2 (FIG. 7. right side) may contain an enrichment site, a calibration site, a barcode for sample multiplexing, or any combination thereof.

Alternatively, the double stranded fragment is ligated to one adaptor where a hairpin molecule is used for the initial extension. For example, where the sequence of the template nucleic acid is known (e.g., amplified nucleic acid or amplicons), a hairpin molecule is used to specifically prime and extend, as well as seal the 3' end of the single stranded nucleic acid using a ligase step (e.g., FIG. 2A-B). For instance, the "asymmetric DNA sample" molecule in FIG. 7 can be generated by extension with the hairpin molecule such that priming and sealing are provided in one step.

While Adaptor 1 would still be used to ligate to the open end of the double stranded template, Adaptor 2 would not be required using this method.

In one other aspect, the methods comprise adding asymmetrical ends to sample nucleic acid to create a non-circular (e.g., linear) template. In another embodiment, different adaptors are used to add the asymmetrical ends. For instance, a unidirectional extension reaction may be performed as described herein using a primer containing a random base region at one end for priming to the single stranded sample nucleic acid and a unique sequence at the other end (see FIGS. 3A-C and 4A-D), thereby preparing the extended fragment for ligation to adaptors. The extension is performed and in one embodiment results in the generation of a double stranded nucleic acid molecule having a single nucleotide 3' overhang (e.g., a single A 3' overhang) and an overhang that comprises a unique sequence. The present invention provides methods for attaching adaptors to each overhang of the extended double stranded molecule. In one embodiment, the method comprises ligating a first adaptor to the extended fragment at the site of the single nucleotide 3' overhang. In another embodiment, the first adaptor comprises a double stranded duplex region having (i) a first overhang region, wherein the first overhang region comprises a single nucleotide overhang that is complementary to the single nucleotide overhang of the extended fragment, and (ii) a second overhang region, wherein the second overhang region comprises a primer site region containing a single primer site, or more than one primer site (e.g., a multi-primer site region) (see Adaptor 1 in FIG. 8A, left side). Alternatively, the first adaptor comprises a double stranded duplex region having (i) a first overhang region comprising a sequence that is complementary to the predetermined unique sequence of the extended fragment as described herein (e.g., see FIGS. 3A-C and 4A-D), and (ii) a second overhang region, wherein the second overhang region comprises a primer site region containing a single primer site, or more than one primer site (e.g., a multi-primer site region) (see Adaptor 1 in FIG. 8B, left side).

Figure 8A:
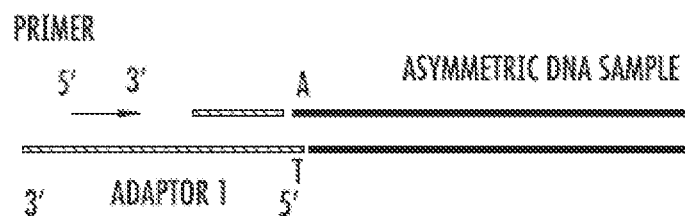
FIGS. 8A-8B depict alternative strategies for creating a linear asymmetric DNA sample fragment with one primer site or multiple primer sites.
Figure 8A:
Figure 8B:
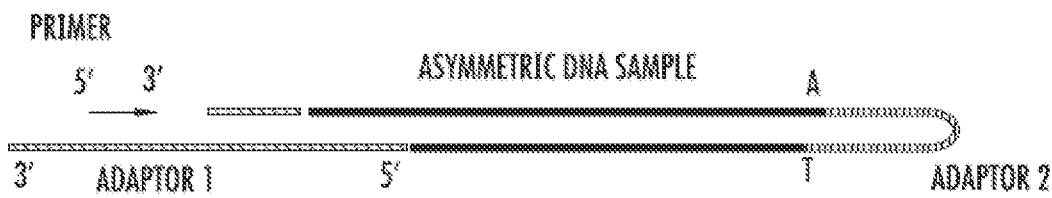
Figure 8B:
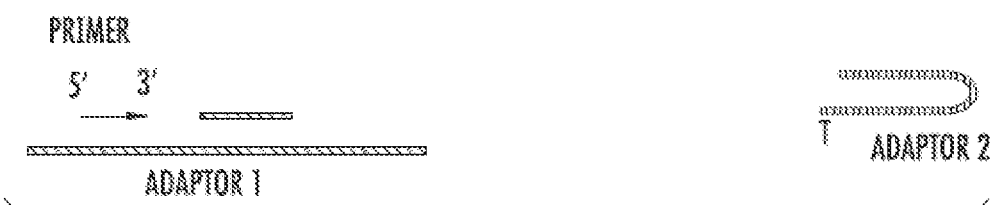

In a preferred embodiment, the first overhang comprises (i) a single T 5' overhang for ligation to a corresponding single A 3' overhang (e.g., found on an extended fragment) as shown in FIG. 8A, or (ii) a 5' overhang sequence that is complementary to the predetermined unique sequence (as shown in FIG. 8B) created as part of a unidirectional extension reaction as described herein (e.g., see FIGS. 3A-C and 4A-D).

In one embodiment, the method comprises the further step (following hybridization) of ligating the first adaptor to the extended fragment.

In another embodiment, the method further comprises ligating a second adaptor to the extended fragment at the site of the single nucleotide overhang or at the site of the unique sequence created as part of a unidirectional extension reaction as described herein (e.g., see FIGS. 3A-C and 4A-D). In other embodiments, the second adaptor comprises a hairpin region and either (i) an overhang region comprising a sequence that is complementary to the predetermined unique sequence of the extended fragment (see Adaptor 2 in FIG. 8A, right side) as described herein, or (ii) an overhang region comprising a single nucleotide overhang that is complementary to the single nucleotide overhang of the extended fragment (see Adaptor 2 in FIG. 8B, right side). In one other embodiment, the second adaptor comprises a hairpin region and an overhang region comprising a single T 3' overhang that is complementary to the single A 5' overhang of the extended fragment (see Adaptor 2 in FIG. 8B).

FIG. 8A-B depict a strategy for creating a linear asymmetric DNA sample fragment. FIG. 8A depicts a strategy using two adaptors on an extended double stranded fragment, which has a single A 3' overhang at one end and a unique sequence at the other end. In one embodiment, the first adaptor (Adaptor 1, FIG. 8A, left side) comprises a double stranded duplex region having an overhang region comprising a primer site region for at least one primer and a single T 5' overhang for ligation. The single T 5' overhang of the first adaptor is ligated to a single A 3' overhang that is present on one end of the extended fragment (from a sample). A second adaptor (Adaptor 2, FIG. 8A, right side) in the form of a hairpin adapter/primer molecule comprising a double stranded duplex region and a hairpin region is ligated to the other end of the extended fragment which comprises a unique sequence. In a preferred embodiment, the second adaptor comprises a region that is complementary to the unique sequence of the fragment molecule at one end and a hairpin region at the other end.

FIG. 8B depicts another strategy using two adaptors on an extended double stranded fragment, which has a single A 3' overhang at one end and a unique sequence at the other end. In one embodiment, the first adaptor (Adaptor 1, FIG. 8B, left side) comprises a double stranded duplex region having a 5' overhang region that is complementary to the unique sequence of the extended fragment and a 3' overhang region that comprises a primer binding region for at least one primer. In one embodiment, the double stranded duplex region is located between the 3' primer binding region and the unique sequence at the 5' overhang. The first adaptor is ligated to the end of the extended fragment which comprises a unique sequence. In another embodiment, a second adaptor is ligated to the single A 3' overhang that is present at the other end of the extended fragment (from a sample). In a preferred embodiment, the second adaptor (Adaptor 2, FIG. 8B, right side) comprises a single T 5' overhang for ligation to the single A 3' overhang of the fragment molecule at one end and a hairpin region at the other end.

Alternatively, the double stranded fragment is ligated to one adaptor where a hairpin molecule is used for the initial extension. For example, where the sequence of the template nucleic acid is known (e.g., amplified nucleic acid or amplicons), a single stranded primed hairpin molecule is used to specifically prime and extend, as well as seal the 3' end of the single stranded nucleic acid using a ligase step (e.g., FIG. 2A-B). For instance, the "asymmetric DNA sample" molecule in FIG. 8A-B can be generated by extension with the hairpin molecule such that priming and sealing are provided in one step. While Adaptor 1 would still be used to ligate to the open end of the double stranded template, Adaptor 2 would not be required using this method.

Single Primer Site Functionality

In one aspect, the functionality provided by the asymmetric ends is priming site functionality. In one embodiment, the present invention provides methods of preparing sample-derived nucleic acid templates having multiple fragments and a single primer site for nanopore sequencing. The addition of a single primer site on a circular or linear nucleic acid sample combined with at least 2 sample fragments in one DNA template improves sequencer throughput and loading efficiency. A sample template with a single primer site reduces the chance of multi-poring at single electrodes on a nanopore array. There is a need to increase the amount of DNA samples read during one run of the instrument and there is a need to have known sequences present in a sample to optionally capture the sample and draw it to the surface of the membrane and increase the array's loading efficiency. This method may also reduce the amount of sample needed to load a chip and reduce the burden of providing large amounts of DNA.

In one embodiment, the present invention provides methods of creating nucleic acid templates for nanopore sequencing which comprise a single primer site. A single primer site provides the benefit that the template will be captured by only one polymerase and pore complex, thereby eliminating the chance that multiple pores may be in contact with a single lipid bilayer membrane.

Multi-Primer Site Functionality

In one other aspect, the present invention provides nucleic acid templates which comprise a multi-primer site region. As described herein, a "multi-priming", "multiple primer", or "multi-primer" site region is a nucleotide sequence comprising at least one and preferably two primer sites adjacent to one another. The multi-priming site region is generally engineered through the use of a suitable adaptor as described here at one end of a sample fragment.

In another aspect, the present invention provides methods for performing extensions of nucleic acid fragments from samples (e.g., open-fold replication) using the multi-primer site region. In one embodiment, the method comprises providing a double stranded nucleic acid molecule in a stem-loop format (see FIG. 4C) wherein the overhang region comprises a multi-primer site region for example in the left hand overhang region of FIG. 4C. In another embodiment, the method further comprises annealing a first primer to a first primer site within a multi-primer site and performing an extension (e.g., open-fold replication). The resulting extension product is a double stranded nucleic acid fragment that can sealed at one end by ligating a hairpin adaptor (see adaptor on the right side in FIG. 4C). In other embodiments, the extension can be repeated with a second primer and second primer site in the multi-primer site region.

Capture Sequence Site Functionality

In one aspect, the functionality provided by the asymmetric ends is capture sequence site functionality. In one embodiment, the present invention provides methods of preparing sample-derived nucleic acid templates having multiple fragments and a capture sequence site for nanopore sequencing. In one embodiment, the capture sequence site is an enrichment site, which comprises a nucleic acid sequence that is complementary to a portion of the sequence of a capture oligonucleotide. The capture oligonucleotide comprises a purification moiety at its 3' end and a sequence that is complementary to the loading capture site at its 5' end. In another embodiment, the capture sequence site is a capture loading site that helps facilitate nanopore sequencing.

Calibration Sequence Functionality

In one embodiment, the functional element is a calibration site. For example, the calibration site may comprise a known nucleic acid sequence of a designated length. In one embodiment, the length is between about 4 and 20 bases. In one preferred embodiment, the length is 8 bases. In another embodiment, a calibration site is designed to be upstream of the unknown template nucleic acid sequence such that it will be read first. The advantage of reading a calibration sequence first is that it allows for calibration of the system using a known nucleic acid sequence prior to reading template from a sample.

Pooling or Multiplex Barcode Functionality

In one other aspect, the functionality provided by the asymmetric ends is a barcode functionality for sample multiplexing purposes. In one embodiment, each nucleic acid fragment from a sample is assigned a unique barcode as a multiplex barcode element in one or both asymmetric ends. In another embodiment, the barcode element comprises a unique double stranded duplex region of between about 8 and about 12 nucleotides. The assignment of a unique barcode to each sample allows for the multiplexing or pooling of different samples in the same sequencing run. Different nucleic acid fragments from different samples can be distinguished using their respective barcodes.

End of Line or "EOL" Functionality

Figure 15A:
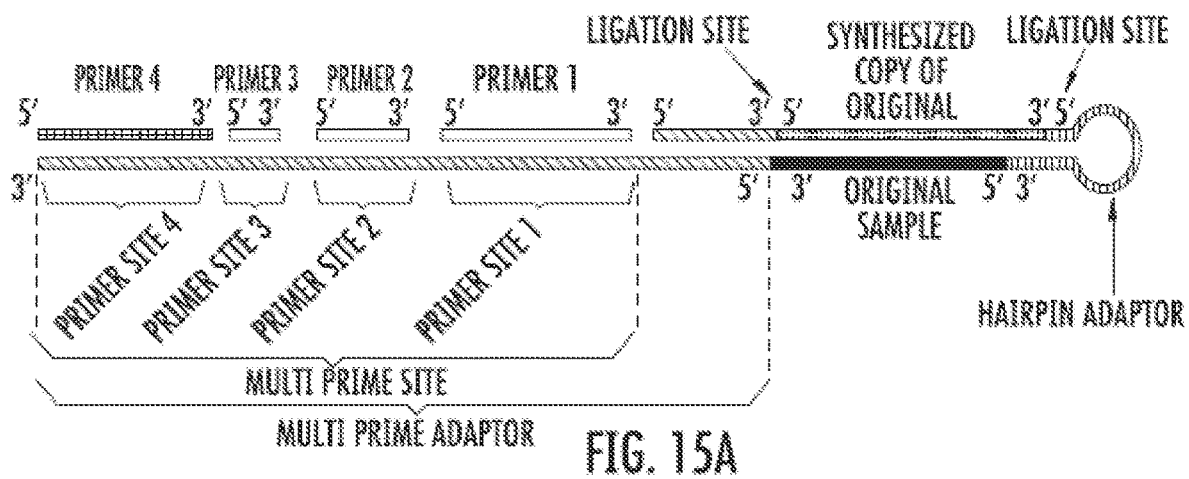
Figure 15B:
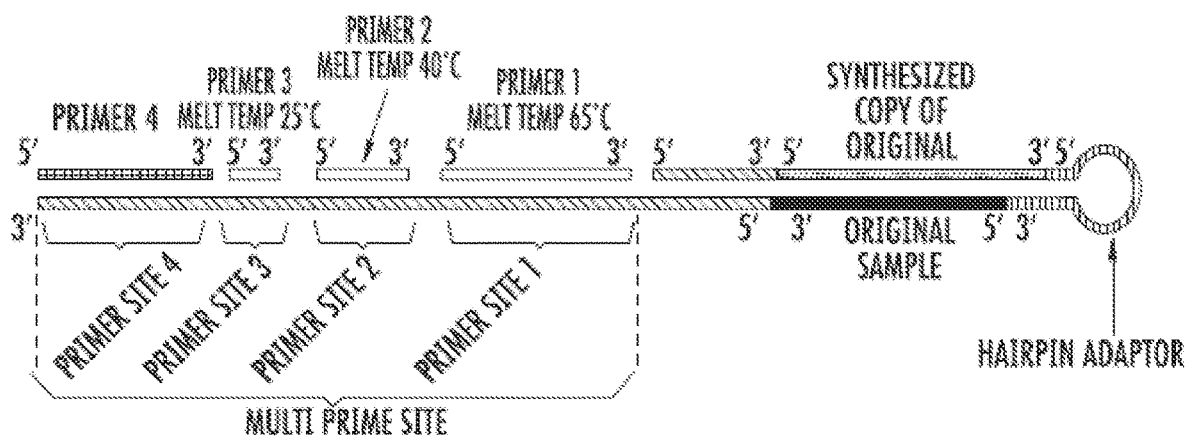
Figure 15D:
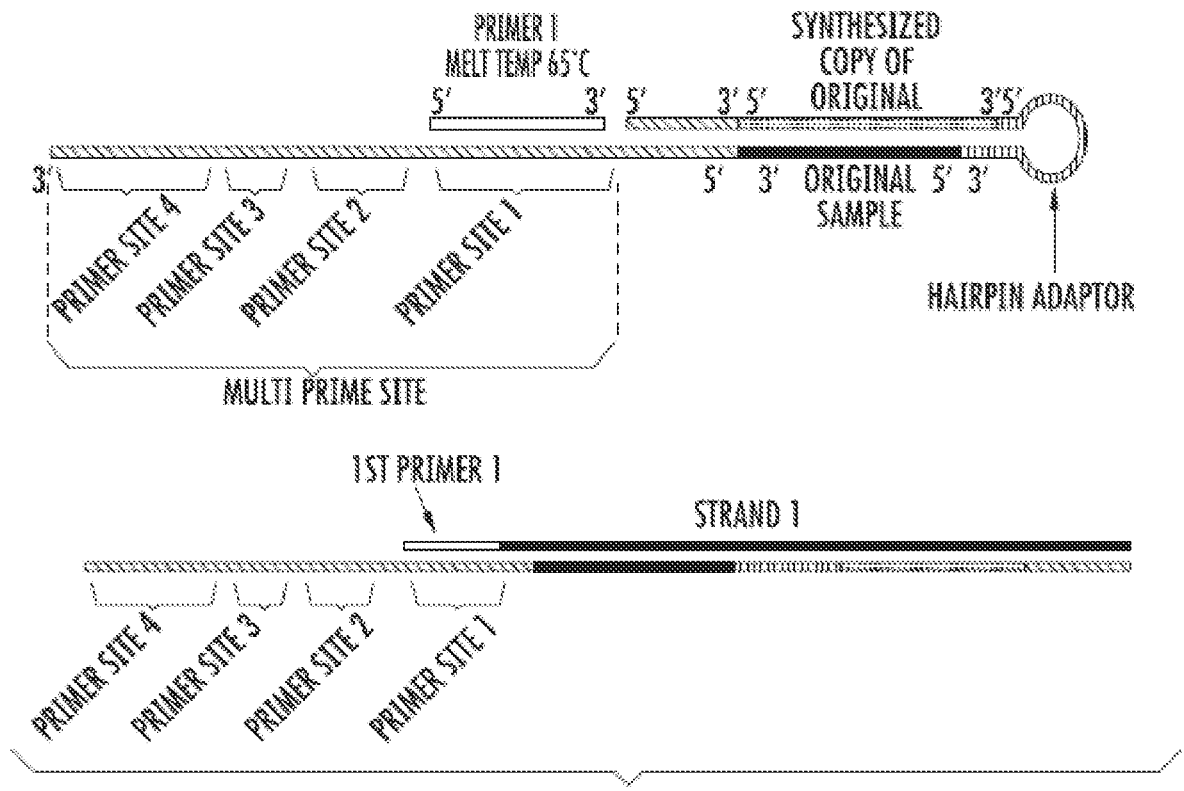
Figure 15D:
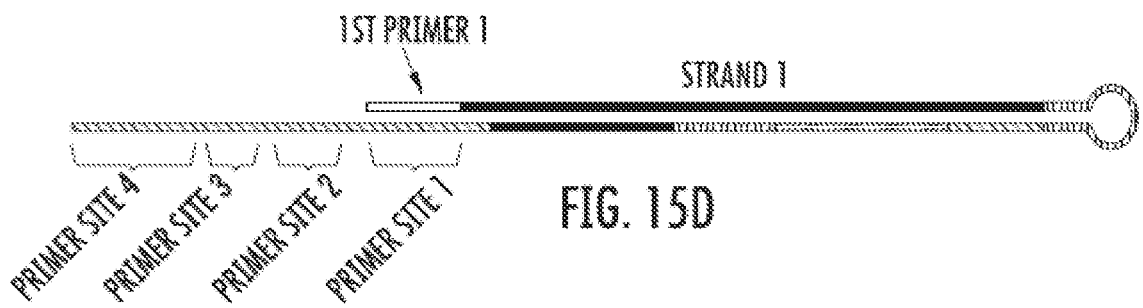
Figure 15E:
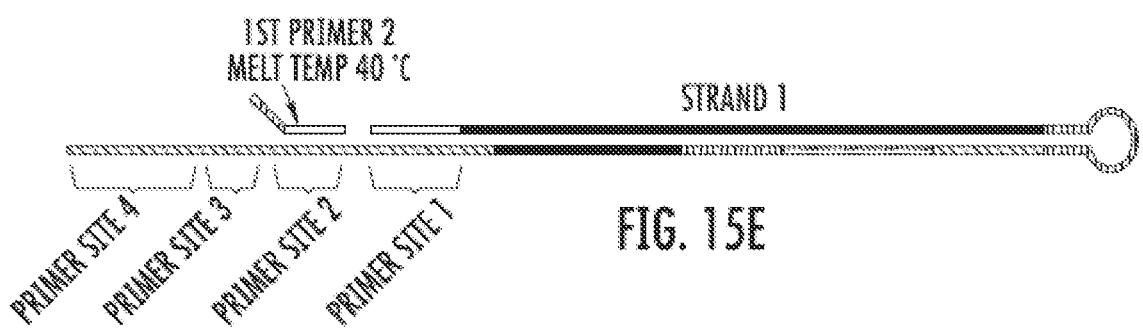
Figure 15F:
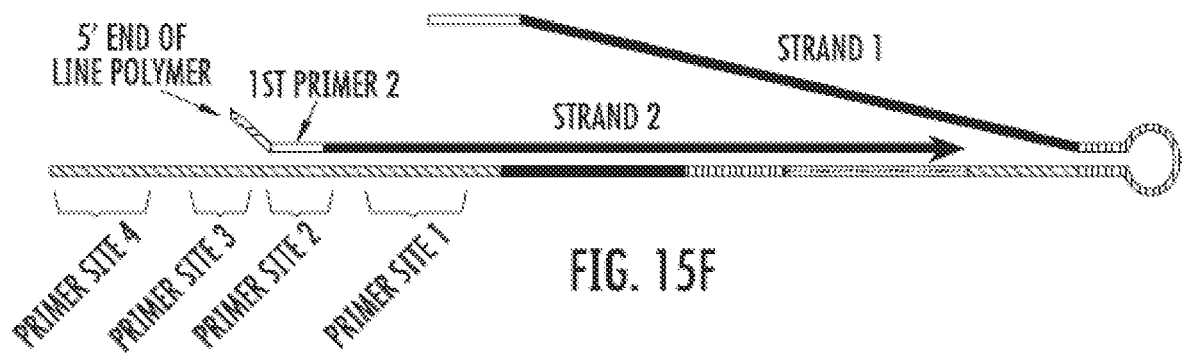

In another aspect, the functionality provided by the asymmetric ends is an "end of line", or "EOL" functionality (see FIG. 15F). As used herein, an "end of line" or "EOL" moiety is a molecular moiety engineered to appear at the 5' most end of a nucleic acid sequence and is readily incorporated into a nucleic acid fragment by engineering it in the 5' non-interacting protein of the last primer used for extension (e.g., open-fold replication). The EOL moiety has properties that make it poorly tolerated by or incompatible with a polymerase. The EOL moiety therefore encourages a polymerase associated with the nucleic acid template in an extension reaction to dissociate itself from the nucleic acid template thereby terminating the extension reaction and making the polymerase available to bind to a new nucleic acid fragment. This feature can provide higher throughput for a sequencing instrument. In one embodiment, the EOL moiety comprises a positively charged moiety. The positive charge is very different from the negatively charged nucleic acid backbone and therefore would facilitate dissociation of the polymerase from the template. In one embodiment, the positively charged moiety comprises spermine. In other embodiments, the EOL moiety is selected from the group consisting of (i) an EOL moiety comprising a nucleic acid strand containing abasic site(s); (ii) an EOL moiety comprising non-naturally occurring nucleotides that do not interact with naturally-occurring nucleotides (e.g., isodG or isodC); and (iii) an EOL moiety comprising PEG or Polyethylene Glycol.

The end of line moiety can be incorporated into a copied or extended sample strand by placing a non-interacting, 5' overhang EOL sequence or fragment on the last primer used for extension of a nucleic acid fragment (e.g., by open-fold replication) from a multi-primer site region. In one embodiment the resulting nucleic acid sample can be left in its linear form and the last primer site in the multi-primer site region can be used as the sequencing by synthesis primer start site. In another embodiment, only the 5' most end of the EOL fragment on the primer may revert back to containing bases (synthetic or natural) that do hybridize or bind to the template strand (see FIG. 17). In this case the EOL primer can be configured to present a blunt end (or an overhang "T" end) at the 5' end of the primer/sample nucleic acid sequence. Subsequently, this end can be ligated to a circular hairpin adaptor that contains a primer sequence for sequencing by synthesis. Additionally, the newly extended double stranded nucleic acid molecule can be circularized to itself, subsequently melted, and primed for sequencing by synthesis.

In another aspect, an EOL element can be provided with a primer that is used for open-fold replication, as described herein. As shown in FIG. 15E-15I, an EOL element may be incorporated into a primer that is complementary to one of the primer sites in a multi-priming site region. In FIG. 15E-15I, this is shown as the 5' element attached to the "1$^{st}$ Primer 2" element. The EOL sequence provides the advantage of creating a polymerase-incompatible region in a linearized or open-folded single strand nucleic acid template wherein upon encountering this incompatible region, the polymerase will dissociate from the template. This leaves the now-free polymerase to bind to another template to begin a new sequencing run.

Figure 17A:
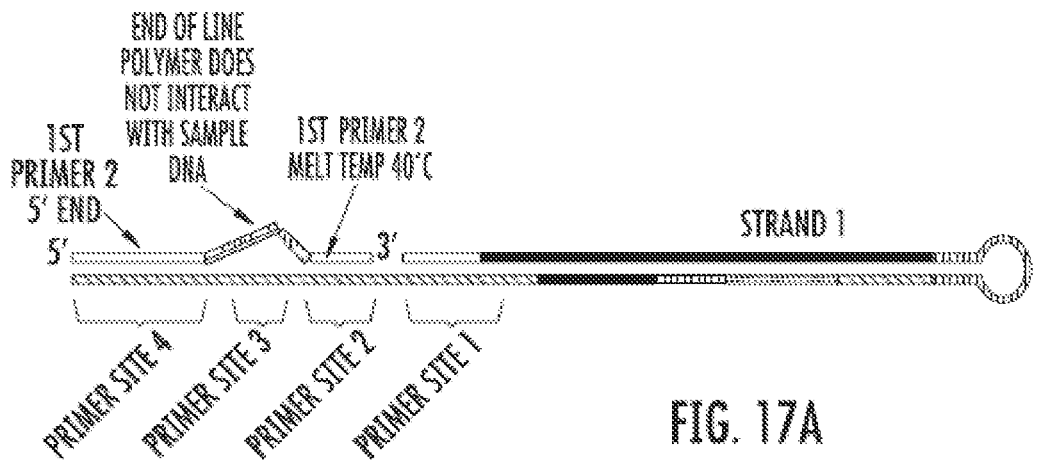
FIGS. 17A-17D depict the use of an end of line moiety as part of an engineered primer in an exemplary strategy for open fold replication.
Figure 17B:
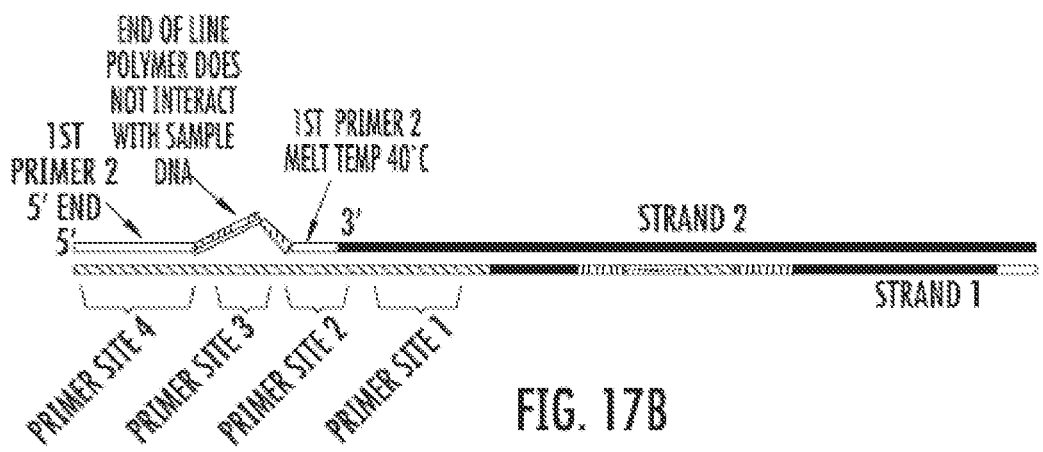
Figure 17C:
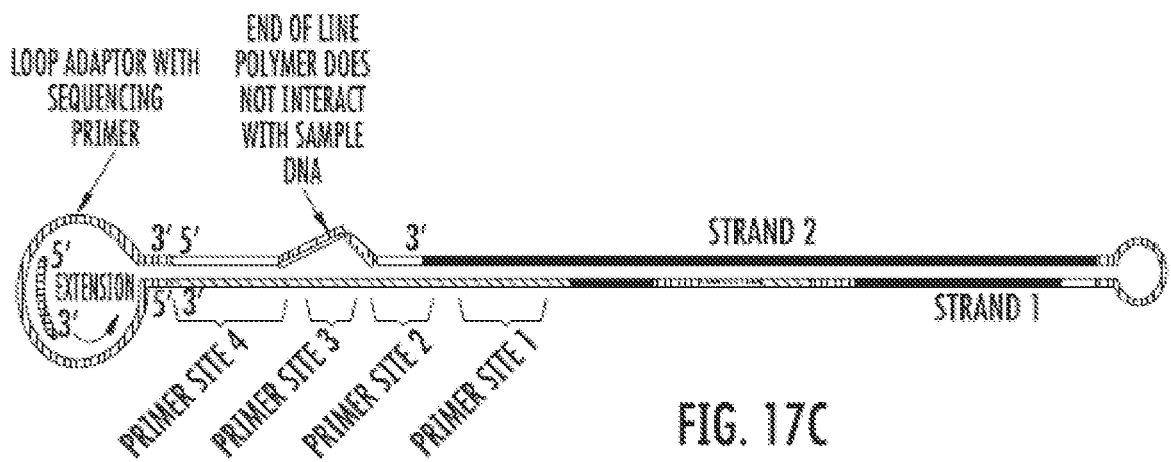
Figure 17D:
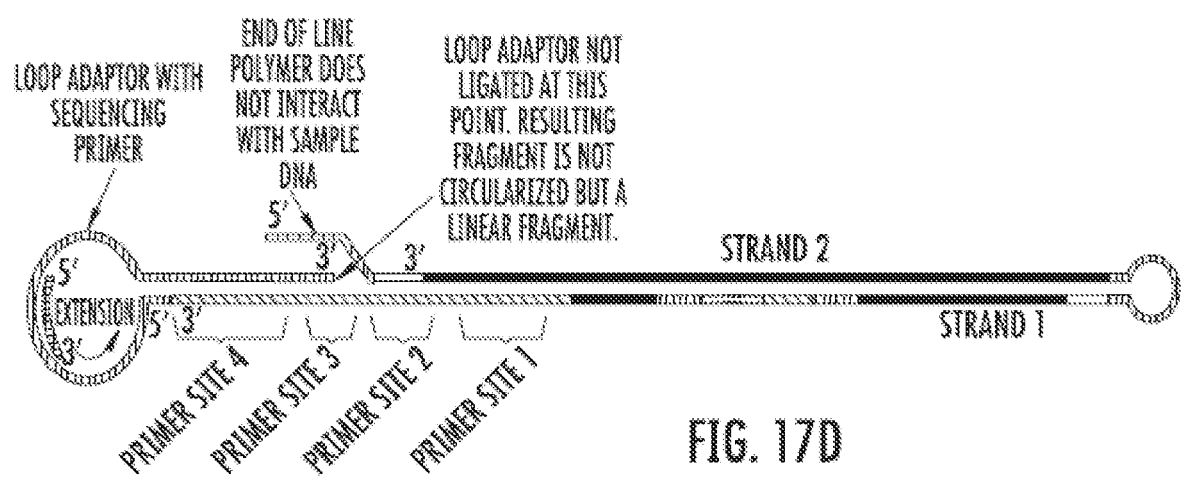

In one aspect, the EOL element is engineered as part of a primer for open fold replication. In one embodiment, the primer comprises a first sequence complementary to a first primer site (e.g., 1$^{st}$ Primer 2 5' end in FIG. 17A), an EOL sequence (e.g., non hybridizing region of the 1$^{st}$ Primer in FIG. 17A), and a second sequence complementary to a second primer site (e.g., Primer Site 2 in FIG. 17A). The EOL sequence (or region) may be positioned to be in proximity to a third primer site (e.g., Primer Site 3 in FIG. 17A) but unable to hybridize because of its engineered incompatibility (e.g., the positive charge of the EOL). In one embodiment, a normal primer (see primer adjacent to Strand 1 in FIG. 17A) is first used to extend a stem-loop molecule as shown in FIG. 17B by open-fold replication, which also shows the incorporated normal primer at the end of the extended fragment. In another embodiment, end loop adaptors may be ligated to each end of the extended fragment to provide a circular concatemer nucleic acid molecule containing the EOL region. In some embodiments, the end loop adaptor comprises a primer for sequencing. Upon initiating a sequencing run, the polymerase will reach the EOL region and cease incorporating nucleotides. Alternatively, the EOL-containing primer may be engineered to have a free-end. In this way, the resulting molecule after open-fold replication is a linear concatemer nucleic acid molecule containing the EOL region (see e.g., FIG. 17C-D).

Adaptor Sequences Between Nucleic Acid Fragments

In another aspect, the adaptors of the present invention, including linking adaptors, adaptors to add asymmetric ends (e.g., to add end loops, overhangs, multi-primer sites, and any other functionality) also provide important identifying information in the context of nucleic acid sequencing. For example, the adaptors are inserted between each nucleic acid fragment (from a sample) in a concatemer molecule as described herein such that they provide an identifying sequence indicating the end (or beginning) of the sequence of a first fragment and/or the beginning (or end) of the sequence of a second fragment. In some embodiment, a method of nucleic acid sequencing comprises the step of sequencing an adaptor nucleic acid sequence as an indicator of the end (or beginning) of the sequence of a first fragment and/or the beginning (or end) of a second fragment. In other embodiments, the method comprises the step of sequencing an adaptor nucleic acid sequence as an indicator of the end (or beginning) of the sequence of a sense strand and/or the beginning (or end) of an antisense strand. In another embodiment, the method comprises detecting the beginning (or end) of the nucleic sequence of a nucleic acid strand (sense and/or antisense) by sequencing an adaptor nucleic acid sequence.

II. Automatic Nucleic Acid Concatemer Formation

In one aspect, the present invention provides concatemer nucleic acid molecules (and methods of making the same) for nucleic acid sequencing, wherein one population of nucleic acid fragments is used. For example, one population of extended fragments with one type of asymmetric ends may be used. In one embodiment, the methods provide for the automatic formation of concatemer nucleic molecules in a circular form. In a preferred embodiment, the methods comprise providing a first population of nucleic acid fragments, e.g., a first population of extended fragments with asymmetric ends, in a single tube. Single nucleic acid templates can be created from original sample fragments in a circular concatemer format using asymmetric ends, wherein the template comprises at least two original sample fragments. In one embodiment, the circular format also comprises a single primer site for nanopore sequencing. In one embodiment, the method comprises adding asymmetrical ends to a sample nucleic acid fragment to create a circular template. In another embodiment, an adaptor is used to generate asymmetrical ends. For instance, a unidirectional extension reaction may be performed as described herein using tailing and a primer containing a random base region at one end for priming to the single stranded sample nucleic acid and a unique sequence at the other end (see FIGS. 3A-C and 4A-D), thereby preparing the extended fragment for ligation to one or more adaptors.

In one embodiment, the method comprises ligating a first adaptor to the extended fragment at an overhang that is complementary to an overhang on the extended fragment. In other embodiments, the overhang comprises (i) a single nucleotide overhang (e.g., a single A 3' overhang); or (ii) a nucleotide sequence that is complementary to a predetermined unique sequence (e.g., a unique sequence that is created as part of a unidirectional extension reaction as described herein). In another embodiment, the first adaptor further comprises a loop region with a single primer site and a double stranded duplex region having the overhang.

In a further embodiment, the double stranded region comprises a single T overhang for ligation to the single A 3' overhang of the extended fragment. The ligation of the first adaptor to the extended fragments provides a population of double stranded template fragments with end loops (e.g., FIG. 10). In additional embodiments, the method further comprises ligating two double stranded template fragments (with end loops) from the population by way of a second adaptor (i.e., a linking adaptor). In one embodiment, the second adaptor comprises a double stranded duplex region having two overhang regions that are each complementary to the remaining overhang of the template fragments (e.g., complementary to the unique sequence provided by the extension primer). In a preferred embodiment, the ligation step results in a circular nucleic acid template comprising two extension fragments separated by the second double stranded (linking) adaptor.

Figure 10:
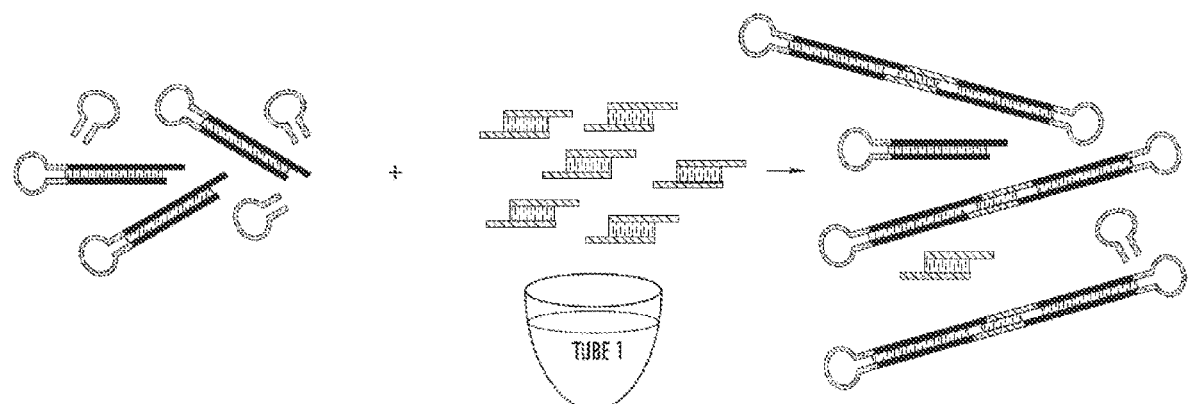
FIG. 10 depicts a first strategy for creating circular nucleic acid concatemers containing multi-sample fragments using nucleic acid sample fragments (with asymmetric ends) and appropriate overhang adaptors to link multiple samples.

FIG. 10 depicts a strategy for creating nucleic acid concatemer circular fragments using asymmetric DNA sample fragments which have a shorter overhang on one end and a longer overhang on the other end. Adaptor 1 (FIG. 10, the adaptor comprising a hairpin structure) is specific to the shorter overhang end and is ligated to create a single primer site. The addition of a second linking nucleic acid adaptor (e.g., a linking dsDNA double stranded adaptor—FIG. 10) allows the fragments to ligate and circularize. The resulting concatemer contains 2 different sample fragments joined in one template separated by a known nucleic acid sequence to allow correct analysis of the two strands.

In another aspect, the present invention provides a method of creating single nucleic acid templates from original sample fragments using asymmetric ends, wherein the template comprises more than two original sample fragments and a single primer site for nanopore sequencing. In one embodiment, the method comprises the concatemerization of small sample fragments that stop at known multiples of sample fragments allowing the system to increase sequencing throughput and maintain accurate analysis for samples consisting of short or medium length DNA or RNA fragments.

Figure 11:
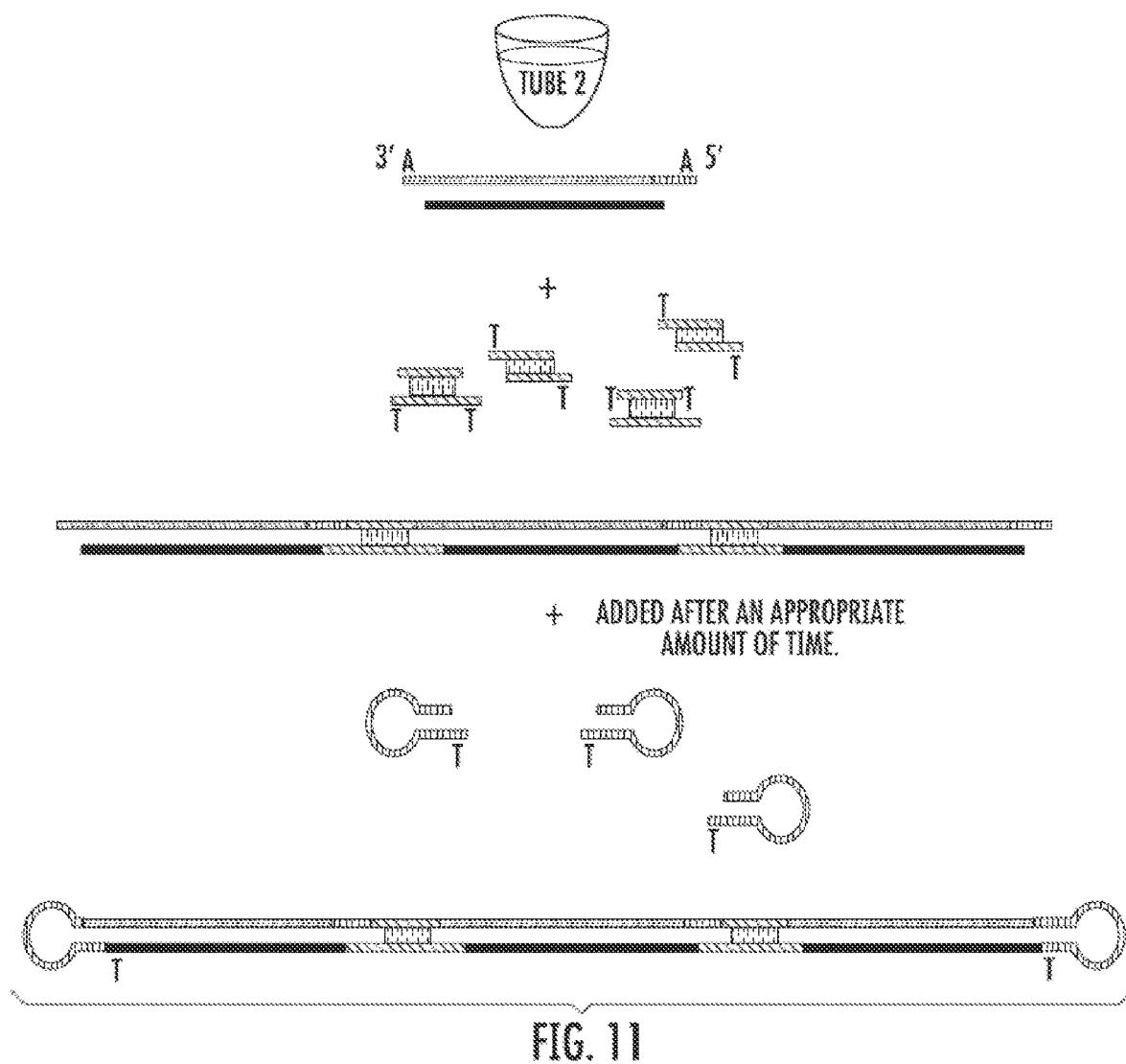
FIG. 11 depicts second strategy for creating circular nucleic acid concatemers containing multi-sample fragments using nucleic acid sample fragments (with asymmetric ends) and appropriate overhang adaptors to link multiple samples.

FIG. 11 depicts another strategy for creating nucleic acid concatemer circular fragments using nucleic acid fragments with asymmetric ends. An extension primer with a one nucleotide 5' overhang is used to make asymmetric double stranded molecules from single stranded nucleic acid template. The resulting double stranded nucleic acid molecules have one end with a single nucleotide 5' overhang (e.g., single A 5' overhang) and another end with a single 3' nucleotide overhang (e.g., a single A 3' overhang) after extension. The addition of a first adaptor, such as a linking nucleic acid adaptor (e.g., a linking dsDNA adaptor—FIG. 11) allows the fragments to ligate producing linear concatemer molecules, which contain 2 or more different sample fragments joined in one template separated by a known adaptor nucleic acid sequence to allow correct analysis (i.e., identification of beginning and/or end of each fragment) of the 2 or more strands. In one embodiment, a second adaptor may be ligated to the ends of the linear concatemer. For example, a nucleic acid adaptor comprising a loop region and a double stranded duplex region with an overhang may be ligated to the ends of each linear concatemer thereby providing circular concatemers. In one embodiment, the second adaptor overhang comprises a single nucleotide overhang (e.g., a single T overhang) that is complementary to the single nucleotide overhang on the ends of each concatemer molecule. In other embodiments, the second adaptor may further comprise a single primer site, an enrichment site, a calibration site, a barcode for sample multiplexing, or any combination thereof.

In one other aspect, the present invention provides circular concatemer nucleic acid molecules (and methods of making the same) for nucleic acid sequencing, wherein at least two populations of nucleic acid fragments are used. For example, a first population of extended fragments with a first type of asymmetric ends and a second population of extended fragments with a second type of asymmetric ends are used. In one embodiment, the methods provide for the automatic formation of concatemer nucleic molecules in a circular form. In a preferred embodiment, the methods comprise providing a first population of nucleic acid fragments, e.g., a first population of extended fragments with first asymmetric ends, in a first tube, and a second population of nucleic acid fragments, e.g., a second population of extended fragments with first asymmetric ends, in a second tube.

In one embodiment, the method of creating circular concatemer nucleic acid molecules comprises creating a population of stem-loop nucleic acid molecules from a first population of nucleic acid fragments. In other embodiments, each fragment of the first population comprises a first overhang having a single nucleotide overhang (e.g., a single A overhang) and a second overhang having a predetermined unique sequence (e.g., a unique sequence that is created as part of a unidirectional extension reaction as described herein). In one embodiment, the predetermined unique sequence is a first unique sequence.

In another embodiment, the method further comprises ligating a closed loop adaptor to an overhang of the fragment from the first population. In one other embodiment, the closed loop adaptor comprises an end loop and a double stranded nucleic acid duplex region having (i) a single nucleotide overhang complementary to the first overhang of the fragment in the first population; or (ii) an overhang comprising a nucleotide sequence that is complementary to the second overhang of the fragment in the first population (e.g., a sequence that is complementary to the predetermined unique sequence of that is created as part of a unidirectional extension reaction as described herein). Ligation of the closed loop adaptor provides a population of stem-loop molecules comprising a closed loop, a nucleic acid fragment, and an overhang suitable for attachment to double stranded linear concatemer nucleic acid molecule.

In one other embodiment, the method of creating circular concatemer nucleic acid molecules for nucleic acid sequencing further comprises creating a population of linear double stranded concatemer nucleic acid molecules from a second population of nucleic acid fragments. In other embodiments, each fragment of the second population comprises a first overhang having a single nucleotide overhang (e.g., a single A overhang) and a second overhang having a predetermined unique sequence (e.g., a unique sequence that is created as part of a unidirectional extension reaction as described herein). In one embodiment, the predetermined unique sequence is a second unique sequence that is complementary to the first unique sequence of the stem-loop nucleic acid molecules.

In another embodiment, the method further comprises ligating together at least two fragments via a linking adaptor thereby creating a population of linear concatemer molecules. In one other embodiment, the linking adaptor comprises a double stranded nucleic acid duplex region having two single nucleotide overhangs complementary to the first overhang of the fragment in the second population. Ligation of the at least two fragments using the linking adaptor provides a population of double stranded nucleic acid concatemer molecules comprising two overhang regions that are each complementary to a predetermined unique sequence (e.g., a second unique sequence) that is suitable for ligation to the stem-loop nucleic acid molecule, a first nucleic acid fragment, a linking region, and a second nucleic acid fragment.

In other embodiments, the method of creating circular concatemer nucleic acid molecules for nucleic acid sequencing further comprises combining the population of stem-loop nucleic acid molecules with the population of double stranded nucleic acid concatemer molecules to create a population of circularized nucleic acid concatemer molecules. In one embodiment, the combining step comprises ligating together (i) the first unique sequence overhang of a first stem loop molecule with one of the second unique sequence overhangs of a concatemer molecule; and (ii) the first unique sequence of a second stem loop molecule with the other second unique sequence overhang of the concatemer molecule, thereby providing a circularized concatemer nucleic acid molecule. In another embodiment, the circularized concatemer molecule comprises a first closed loop end, four nucleic acid fragments having their respective sense and antisense strands, and a second closed loop end.

Figure 12:
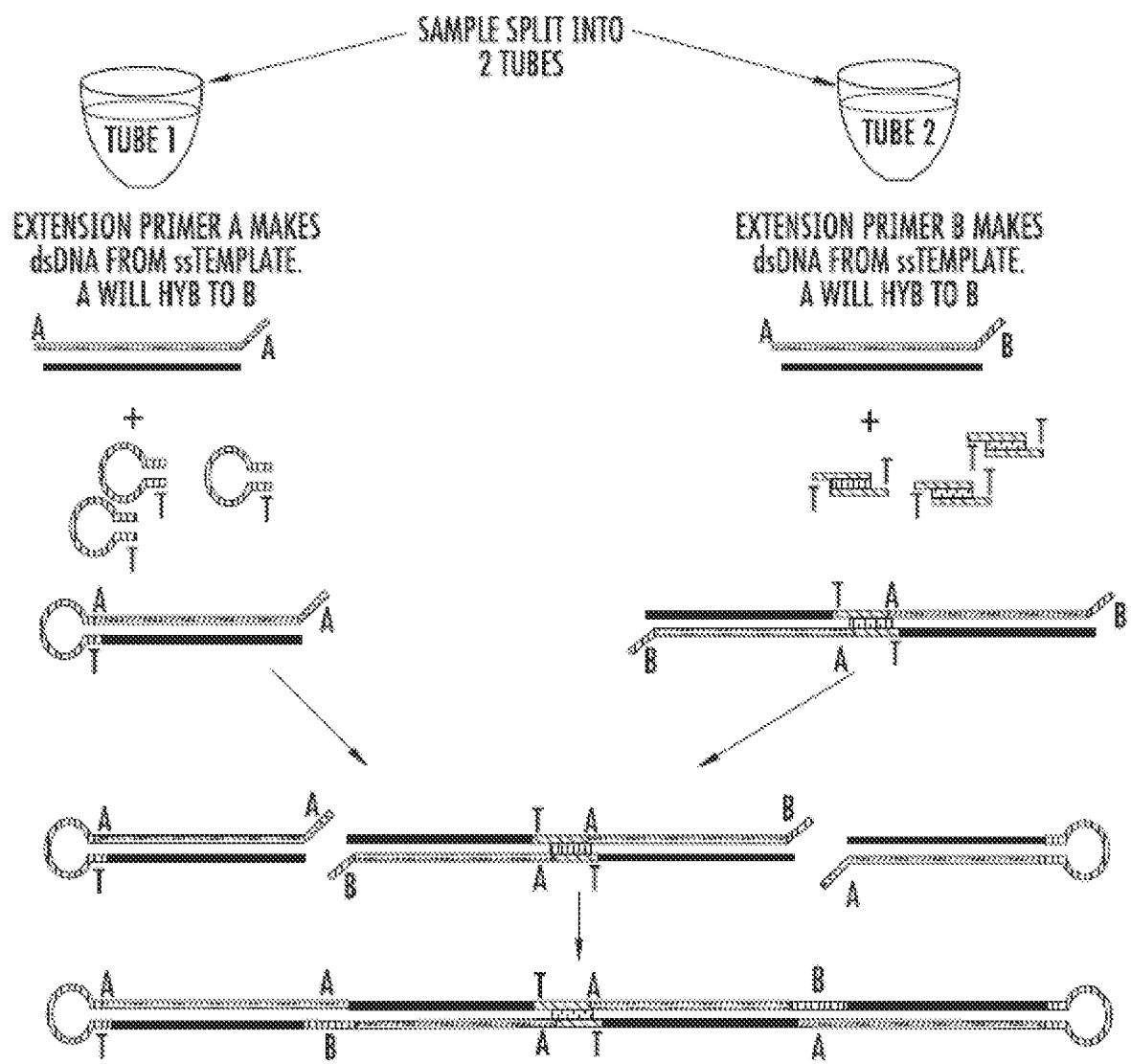
FIG. 12 depicts a third strategy for creating circular nucleic acid concatemers containing multi-sample fragments using nucleic acid sample fragments (with asymmetric ends) and appropriate overhang adaptors to link multiple samples.

FIG. 12 depicts a strategy for creating circular nucleic acid concatemer molecules containing multi-sample fragments using nucleic acid sample fragments (with asymmetric ends) and appropriate overhang adaptors to link multiple samples.

III. Step-Wise Nucleic Acid Concatemer Formation

In another aspect, the present invention provides linear concatemer nucleic acid molecules (and step-wise or programmable methods of forming the same). For instance, a method of forming linear concatemer molecules comprises the step of open-fold replication, and/or wherein at least two populations of nucleic acid fragments are used. For example, a first population of extended fragments with a first type of asymmetric ends and a second population of extended fragments with a second type of asymmetric ends are used. In one embodiment, the methods provide for the step-wise formation of concatemer nucleic molecules in a linear form. In a preferred embodiment, the methods comprise providing a first population of nucleic acid fragments, e.g., a first population of extended fragments with first asymmetric ends, in a first tube, and a second population of nucleic acid fragments, e.g., a second population of extended fragments with second asymmetric ends, in a second tube.

For example, one population of extended fragments with one type of asymmetric ends may be used. In one embodiment, the methods provide for the step-wise formation of concatemer nucleic molecules in a linear form. In a preferred embodiment, the methods comprise providing a first population of nucleic acid fragments, e.g., a first population of extended fragments with asymmetric ends, in a single tube. In one embodiment, the method comprises adding asymmetrical ends to a sample nucleic acid fragment to create a linear template. In another embodiment, an adaptor is used to generate asymmetrical ends. For instance, a unidirectional extension reaction may be performed as described herein using tailing and a primer containing a random base region at one end for priming to the single stranded sample nucleic acid and a unique sequence at the other end (see FIGS. 3A-C and 4A-D), thereby preparing the extended fragment for ligation to one or more adaptors.

In one embodiment, the method of creating linear concatemer nucleic acid molecules further comprises creating a population of double stranded single fragment nucleic acid molecules from a first population of nucleic acid fragments. In other embodiments, each fragment of the first population comprises a first overhang having a single nucleotide overhang (e.g., a single A overhang) and a second overhang having a predetermined unique sequence (e.g., a unique sequence that is created as part of a unidirectional extension reaction as described herein). In one embodiment, the predetermined unique sequence is a first unique sequence.

In another embodiment, the method further comprises ligating an adaptor to the second overhang of the fragment from the first population. In one other embodiment, the adaptor comprises a double stranded nucleic acid duplex region having (i) a first overhang comprising a nucleotide sequence that is complementary to the second overhang of the fragment in the first population (e.g., a sequence that is complementary to the predetermined unique sequence of that is created as part of a unidirectional extension reaction as described herein); and (ii) a second overhang comprising a functional element. In one embodiment, the functional element is a primer site region or a multi-primer site region. Ligation of the adaptor provides a population of double stranded single fragment nucleic acid molecules comprising the first overhang having a single nucleotide overhang, a nucleic acid fragment, and an overhang comprising a functional element.

In one embodiment, the method of creating linear concatemer nucleic acid molecules further comprises creating a population of stem-loop nucleic acid molecules from a second population of nucleic acid fragments. In other embodiments, each fragment of the second population comprises a first overhang having a single nucleotide overhang (e.g., a single A overhang) and a second overhang having a predetermined unique sequence (e.g., a unique sequence that is created as part of a unidirectional extension reaction as described herein). In one embodiment, the predetermined unique sequence is a second unique sequence. For instance, the second unique sequence is different from the first unique sequence of the population of double stranded single fragment nucleic acid molecules.

In another embodiment, the method further comprises ligating a closed loop adaptor to an overhang of the fragment from the second population. In one other embodiment, the closed loop adaptor comprises and end loop and a double stranded nucleic acid duplex region having an overhang comprising a nucleotide sequence that is complementary to the second overhang of the fragment in the first population (e.g., a sequence that is complementary to the predetermined unique sequence of that is created as part of a unidirectional extension reaction as described herein). In additional embodiments, the method further comprises ligating another adaptor comprising a double stranded duplex region and two single nucleotide overhangs complementary to the first overhang of the population of double stranded single fragment nucleic acid molecules. The ligation of the closed loop adaptor and the double stranded duplex adaptor provides a population of stem-loop molecules comprising a closed loop, a nucleic acid fragment, and a single nucleotide overhang that is complementary to the first overhang (i.e., single nucleotide overhang) on the population of double stranded single fragment nucleic acid molecules.

In other embodiments, the method of creating linear concatemer nucleic acid molecules for nucleic acid sequencing further comprises combining the population of double stranded single fragment nucleic acid molecules with the population of stem-loop nucleic acid molecules to create a population of linear nucleic acid concatemer molecules. In one embodiment, the combining step comprises ligating together (i) the first overhang (i.e., single nucleotide overhang) on the population of double stranded single fragment nucleic acid molecules, and (ii) the single nucleotide overhang of the population of stem-loop nucleic acid molecules, thereby providing the population of linear nucleic acid concatemer molecules. In another embodiment, the linear concatemer molecule comprises a first overhang comprising the functional element (e.g., a primer site region or multi-primer site region), a first and second nucleic acid fragment having their respective sense and antisense strands, and a closed loop end.

Figure 13:
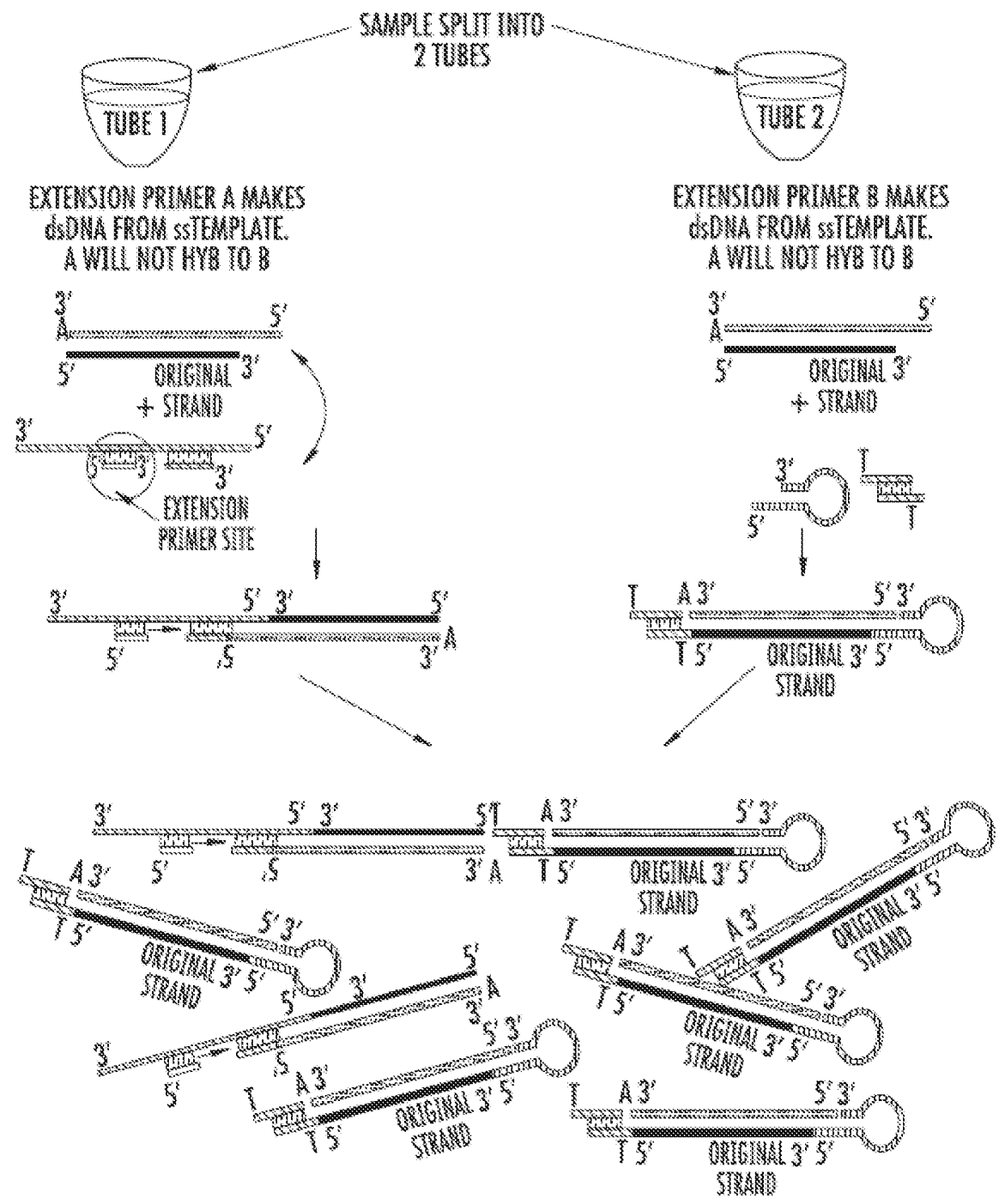
FIG. 13 depicts a first strategy for creating linear nucleic acid concatemers containing multi-sample fragments using nucleic acid sample fragments (with asymmetric ends) and appropriate overhang adaptors to link multiple samples. The strategy depicted exemplifies the automatic creation of a 2 sample, linear, nucleic acid concatemer and also illustrates the mixing of a larger concentration of hairpin sealed nucleic acid fragments so that primers on a multi-priming site region on the primer strand can perform replication of the sample strand and newly ligated hairpin strands and subsequently stepwise concatemerization of another hairpin sealed nucleic acid fragment.

FIG. 13 depicts a strategy for creating linear nucleic acid concatemer molecules containing multi-sample fragments using nucleic acid sample fragments (with asymmetric ends) and appropriate overhang adaptors to link multiple samples. As shown, the resulting linear concatemer molecule may be subjected to a further extension to make copies, such as by open-fold replication, of the two nucleic acid fragments.

Figure 14A:
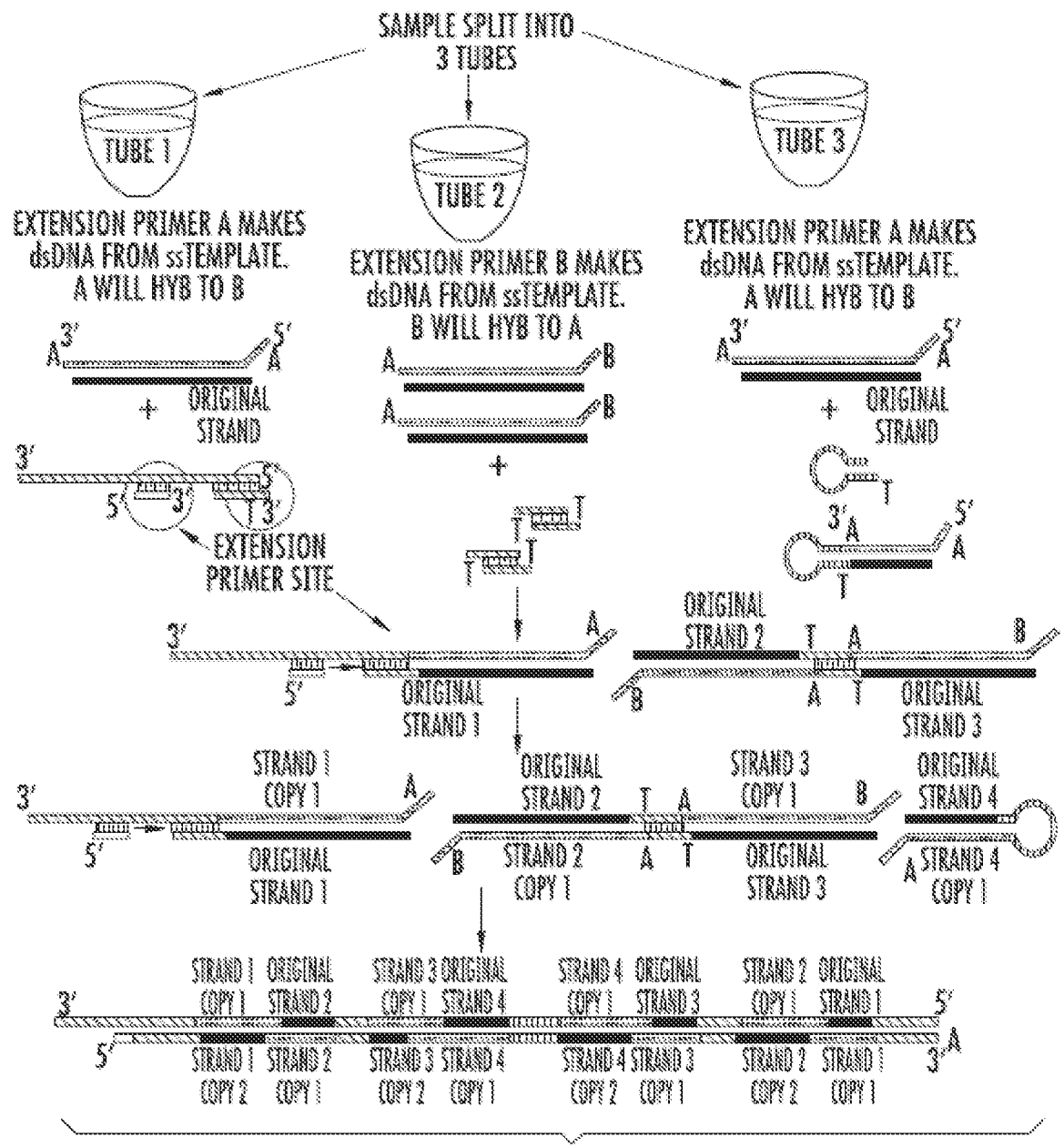
FIGS. 14A-14C depict a second strategy for creating linear nucleic acid concatemers containing multi-sample fragments using nucleic acid sample fragments (with asymmetric ends) and appropriate overhang adaptors to link multiple samples. The strategy depicted exemplifies the automatic creation of a four-sample, linear, nucleic acid concatemer using asymmetric DNA sample fragments and appropriate T overhang adaptors to link the two samples.
Figure 14B:
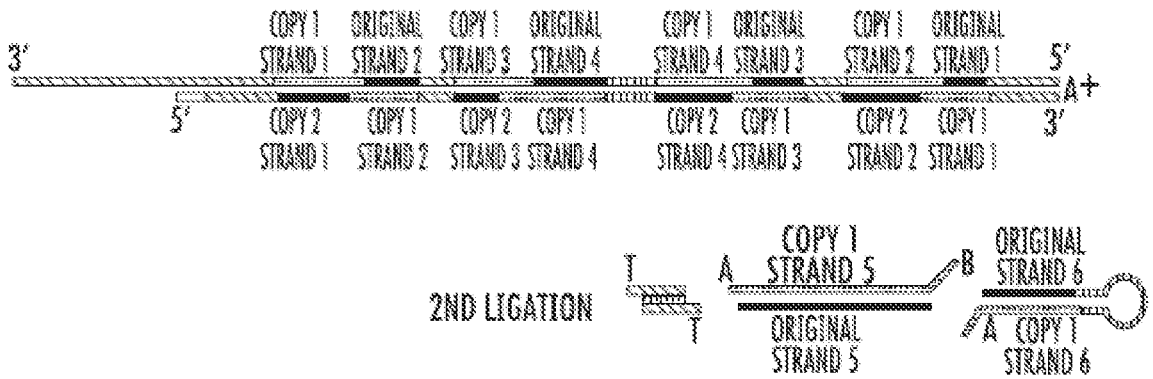
Figure 14B:
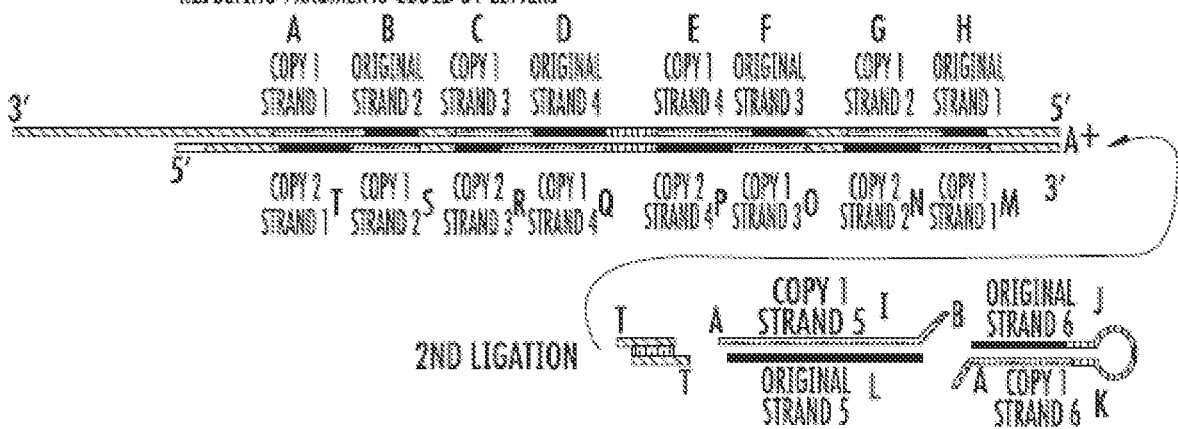
Figure 14C:
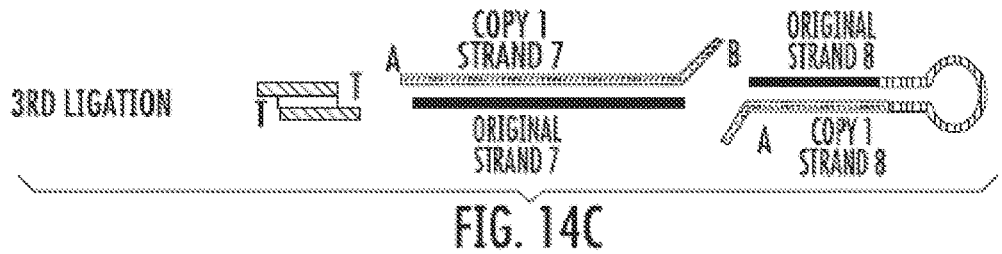

In another aspect, the present invention provides linear concatemer nucleic acid molecules (and step-wise or programmable methods of forming the same). For instance, a method of forming linear concatemer molecules comprises the use of at least three populations of nucleic acid fragments (and optionally open-fold replication). A first population of extended fragments with a first type of asymmetric ends, a second population of extended fragments with a second type of asymmetric ends, and a third population of extended fragments with a third type of asymmetric ends are used. In one embodiment, the methods provide for the step-wise formation of concatemer nucleic molecules in a linear form. In a preferred embodiment, the methods comprise providing a first population of nucleic acid fragments, e.g., a first population of extended fragments with first asymmetric ends, in a first tube, a second population of nucleic acid fragments, e.g., a second population of extended fragments with second asymmetric ends, in a second tube, and a third population of nucleic acid fragments, e.g., a third population of extended fragments with third asymmetric ends, in a third tube. FIGS. 14A-C depict such a strategy for creating linear nucleic acid concatemer molecules containing multi-sample fragments using nucleic acid sample fragments (with asymmetric ends) and appropriate overhang adaptors to link multiple samples. As shown, the resulting linear concatemer molecule may be subjected to a further extension to make copies, such as by open-fold replication, of the multiple nucleic acid fragments.

Nucleic Acid Concatemer Molecules and Sequencing

For nanopore sequences, there are advantages associated with the creation of single nucleic acid molecules having a known number of concatemerized samples including higher throughput and multiple-pass read accuracy in a linear molecule. In addition, a linear or circular molecule can provide a known EOL (end-of-line) sequence to encourage the enzyme to drop the template and free itself to sequence another sample.

In one aspect, the present invention provides methods of making concatemers comprising multiple nucleic acid fragments from a sample. In one embodiment, each fragment of the concatemer is separated from its neighboring fragment(s) by a known sequence, which distinguishes each fragment. In another embodiment, the methods comprise the use of adaptors to ligate different fragments together, wherein the adaptors comprise the known sequence. In one other embodiment, the methods comprise the step wise concatemerization of a known number of sample fragments. Step wise concatemerization comprises the use of at least two different reactions to generate extended double stranded fragments from the original sample. In this way, the number of fragments that are provided in the concatemer can be predetermined. In an additional embodiment, the method comprises the step of duplicating the fragments. The making of copies of the sample fragments provides the benefit of increasing sequencing throughput and maintaining accurate analysis for samples.

The sealing of a DNA sample strand at the end opposite the primer site from the multi-priming site region by ligating a new hairpin adaptor, and the subsequent extension of the same DNA sample by performing a single cycle of enzymatic extension (open-fold replication) from a second, third, fourth, or greater than 4/new primer in the multi-primer site, can be repeated as often as the number of multi-primer sites allows and as many times as the operator desires. The result is a single nucleic acid molecule with multiple copies of the same original sample nucleic acid fragment. An additional novel feature of the multi-primed, open-fold replication technique is that the primers and individual primer sites in the multi-primer site can be selected so that the primer binding affinity is different for each primer. One primer and primer site (primer 1) (the furthest from the 5' end of the sample molecule) may have a melting temperature of 40 deg C. while the next prime closer to the 5' end of the sample molecule (primer 2) may have a melting temperature of 25 deg C. By setting the temperature during a one tube enzymatic extension and enzymatic ligation reaction to 35 deg C. at the start, only primer 1 will hybridize to the primer site and will then extend to the end of the sample. After the extension an adaptor; profiled to match and bind to the newly extended end (A tail if Klenow or Taq polymerase are used), is ligated by the ligase to the new free end. After waiting an appropriate time for the above reaction to occur, the temperature is dropped and primer 2 will now bind in the multi-priming site and promptly will be extended to the end of the DNA sample. Once again the newly created A tailed end will quickly be ligated to an existing T tailed adaptor present in the reaction mix. This process can be repeated for many temperature dependent primers and therefore many open-fold replication cycles. For example if 7 base primers are selected to separately bind at every 5 deg C., then 7 different primers can be sequentially activated and extended on one 63 base multi-prime site overhang. The open-fold replication technique doubles the number of copies of any sample fragment in the molecule every cycle. Therefore, starting with one 46 base pair duplex sample and a hairpin adaptor consisting of 14 bases, seven open-fold replications will result in a 128 single stranded copies of the original duplex and contain approximately 7,680 bases. The single tube, hands-free operation of the open-fold replication technique is simpler and reduces sample handling errors and is saves considerable hands on time.

Multi-Primer Site Functionality in Nucleic Acid Extensions

A multi-primer site provides advantages for nucleic acid extensions, as described herein. In one aspect, open-fold replication methods of the present invention allow one primer site of the multi-priming site region to be used for multiple replications. In one embodiment, the open-fold replication method comprises performing a first replication with a first primer site. The resulting nucleic acid molecule comprises a double stranded duplex region, including the first primer site and the first primer, which is then contacted with an excess of the first primer at a temperature sufficient to disrupt the double stranded duplex region such that it is rendered single stranded (i.e., denaturing conditions) in the presence of a thermostable polymerase. There will be competition for the first primer site (which is now exposed on the single strand due to the denaturing conditions) between the extramolecular excess of first primer and the intramolecular sequence located at the other end of the single stranded molecule (which is the incorporated first primer from the initial open-fold replication). Under suitable conditions, it is expected that the extramolecular excess of the first primer will outcompete the intramolecular sequence, thereby leading to re-priming of the first primer site by the first primer. For example, following the initial open-fold replication, the product is flash-cooled to at least room-temperature before adding the excess of first primer. This provides the advantage of using the same primer site multiple times for open-fold replication.

In another aspect, the multi-primer site region comprises at least a first primer site having a first melting temperature and a second primer site having a second melting temperature. Upon hybridization to their corresponding primer(s), multiple primer sites having different melting temperatures provide certain advantages. For instance, the different melting temperatures may be used to sequentially facilitate hybridization of one primer at a time. In one embodiment, a first melting temperature is used to bind a first primer to a first primer binding site and extend it by replication (e.g., open-fold replication). In another embodiment, a subsequent replication is performed where a second melting temperature is used to bind a second primer to a second primer binding site and extend it by replication (e.g., open-fold replication). In a preferred embodiment, the first melting temperature is higher or lower than the second melting temperature. Those of ordinary skill in the art will appreciate that additional primer sites (e.g., third, fourth, fifth, etc.) having additional melting temperatures (e.g., third, fourth, fifth, etc.) may be used.

FIG. 15A-I provide an exemplary strategy for the use of a multi-primer region site having primer sites with different melting temperatures. FIG. 15A shows a stem-loop nucleic molecule containing a multi-primer adaptor containing multi-primer sites (Primer Sites 1-4) ligated to a nucleic acid fragment (e.g., from a sample for nanopore sequencing). FIG. 15B shows the different melting temperatures for primers in the multi-primer site (Primers 1-3). The variation in melting temperature allows for the sequential loading of primers.

In one embodiment, the melting temperature difference between primers is about 10 degrees Celsius, about 12 degrees Celsius, about 15 degrees Celsius, about 17 degrees Celsius, about 20 degrees Celsius, about 22 degrees Celsius, about 25 degrees Celsius, about 27 degrees Celsius, about 30 degrees Celsius, about 32 degrees Celsius, about 35 degrees Celsius, about 37 degrees Celsius, about 40 degrees Celsius, about 42 degrees Celsius, about 45 degrees Celsius, or about 50 degrees Celsius. In other embodiments, the melting temperature difference between primers is 15 degrees Celsius, 25 degrees Celsius, or 40 degrees Celsius.

In other embodiments, the melting temperature of each primer is selected from the group consisting of about 20 degrees Celsius, about 22 degrees Celsius, about 25 degrees Celsius, about 27 degrees Celsius, about 30 degrees Celsius, about 32 degrees Celsius, about 35 degrees Celsius, about 37 degrees Celsius, about 40 degrees Celsius, about 42 degrees Celsius, about 45 degrees Celsius, about 47 degrees Celsius, about 50 degrees Celsius, about 52 degrees Celsius, about 55 degrees Celsius, about 57 degrees Celsius, about 60 degrees Celsius, about 62 degrees Celsius, about 65 degrees Celsius, about 67 degrees Celsius, and about 70 degrees Celsius.

FIG. 15C depicts the hybridization of a first primer (Primer 1) with a melting temperature of 65 degrees Celsius to Primer Site 1 (within the Multi-Primer site region) and the resulting extension product of open-fold replication. The extended product includes a double stranded nucleic acid fragment comprising the original template strand having the original sample and synthesized copy of the original and a new strand (Strand 1) that is a copy of the template strand.

FIG. 15D shows the attachment of a circular hairpin adaptor (FIG. 15D, right side) by ligation to the newly created end (i.e., blunt or 3' single nucleotide, e.g., single A, overhang end of the open fold replication product. FIG. 15E shows the hybridization of a second primer (Primer 2) at a second melting temperature of 65 degrees Celsius to Primer Site 2. In some embodiments, the second primer has a polymer sequence on the 5' that does not interact with sample DNA. The 5' overhang contains elements that are not natural for the polymerase to use as template and this encourages the dissociation of the polymerase from the template. This is referred to as the EOL polymer, or End of Line polymer as described herein.

Figure 15G:
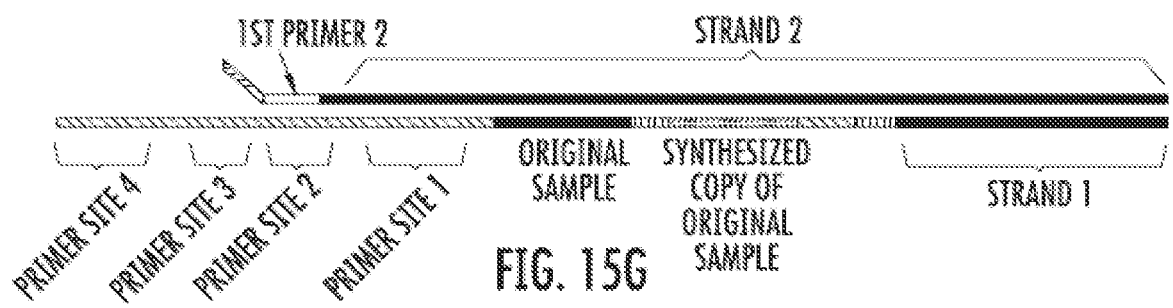

FIG. 15F depicts the extension (by open-fold replication) of Primer 2, thereby creating Strand 2. FIG. 15G provides an example of an extended product (via Primer 2) using open-fold replication. The extended product includes a double stranded nucleic acid fragment comprising a concatemer strand containing the template strand region (the original sample and the synthesized copy of the original sample) and corresponding copy from FIG. 15C (designated as Strand 1 in FIG. 15G), and a corresponding copy as the other strand (Strand 2 in FIG. 15G).

Figure 15H:
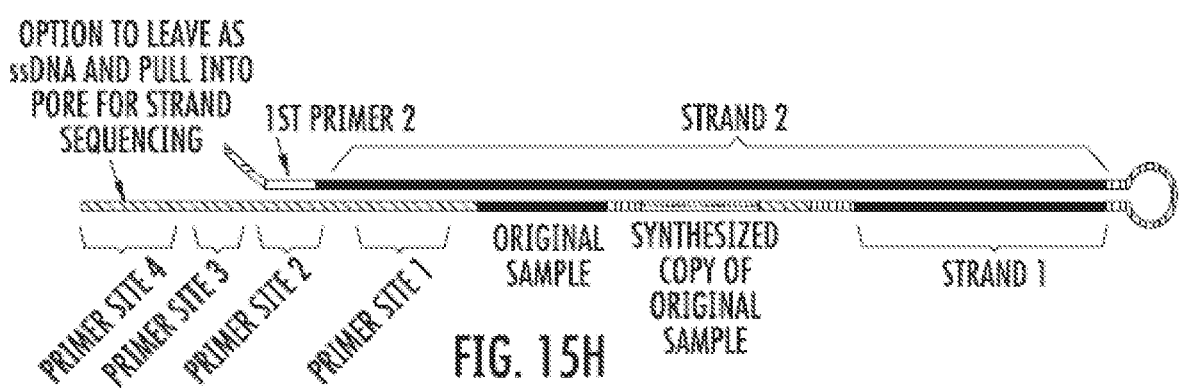
Figure 15I:
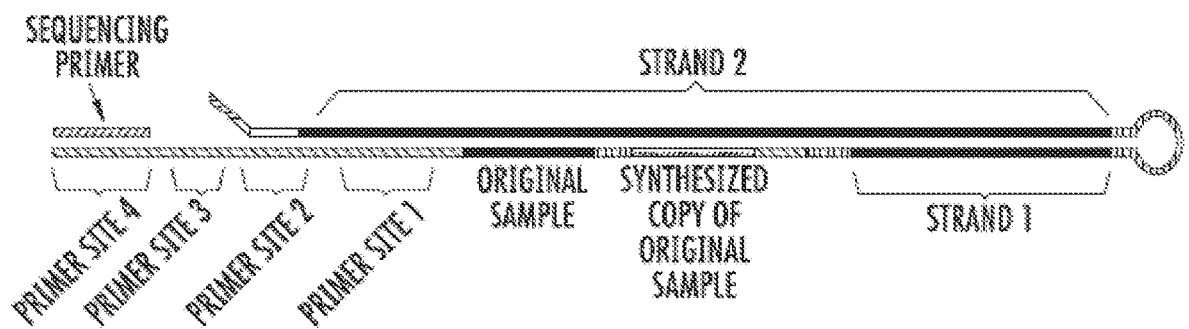

FIG. 15H depicts the ligation of a hairpin adaptor (FIG. 15H, right side) to seal the newly created end of the product of this cycle of open fold replication. The steps depicted in FIGS. 15C-H can be repeated multiple times as long as there is the possibility of hybridizing another primer in the multi-priming site. All steps may optionally be performed in an automated fashion with all reagents in one tube and temperature used to moderate the correct primer binding and extension. It is also understood that the hairpin primer that is illustrated in these drawings can be replaced at any time by a separate, different double stranded sample nucleic acid closed at one end with a hairpin adaptor and presenting either a blunt end or 3' single nucleotide (e.g., single T) tail overhang appropriate to ligate to the end of the newly created product of the open fold replication step. This results in a concatemer and by repeating this open loop replication and ligation at the newly created end multiple times, multiple different sample fragments are ligated and replicated. FIG. 15I depicts the binding of a sequencing primer for sequencing by synthesis. This linear molecule contains multiple reads of the same fragment and an EOL sequence.

In another aspect, the present invention provides methods for the use of the same primer site within a multi-primer site region. For instance, the method concerns the re-use of a first primer with a corresponding first primer site after an initial replication (e.g., open-fold replication) has been performed with a first population of the first primer on the first primer site. In general, the re-use of the first primer with the first primer site is performed by (i) repeated heating (e.g., to 95° C.) to dissociate the double stranded duplex nucleic acid molecule to form single stranded nucleic acid, and (ii) reducing the temperature in the presence of a second population of the first primer such that the second population of the first primer hybridizes to the available first primer site (e.g., a temperature approximately 3-5° C. below the melting temperature of the first primer). In addition, the second population of the first primer is provided in excess to allow it to compete for binding to the now available first primer site on the single stranded nucleic acid. Following hybridization of the second population of the first primer to the single stranded molecule, another extension is performed (e.g., open fold replication).

By varying temperature in an automated fashion in both of the above methods, the primer hybridization, open fold replication, ligation of either a new single closed-end adaptor or an entirely new, different single closed-end sample fragment (concatemerization) can be accomplished with all reagents in one reaction tube and with little or no manual intervention. By varying the temperature with little or no manual intervention, the process may be repeated for one to many multiple cycles of priming, open fold replication, and ligation of new adaptor or DNA fragment. This greatly simplifies the sample preparation process. In another embodiment, the methods of the present invention include manual intervention steps, such as the manual addition of specific primers, nucleic acid samples, or other reagents.

Figure 16A:
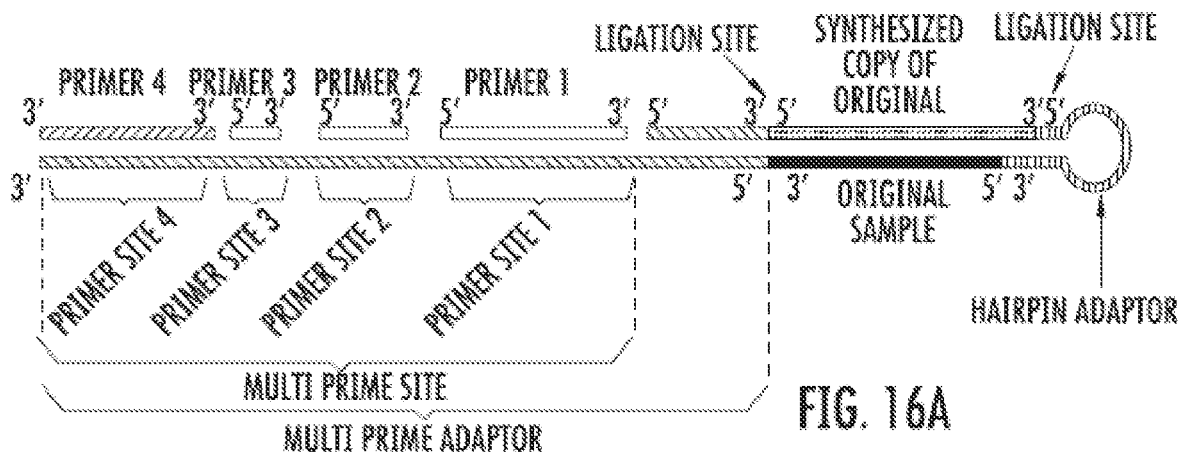
FIGS. 16A-16I depict another strategy for using a multi-primer adaptor site at one end of a sample nucleic acid molecule while having a sealed adaptor at the other end of the molecule. A single site from the multi-primer adaptor site may be used more than once for replication.
Figure 16B:
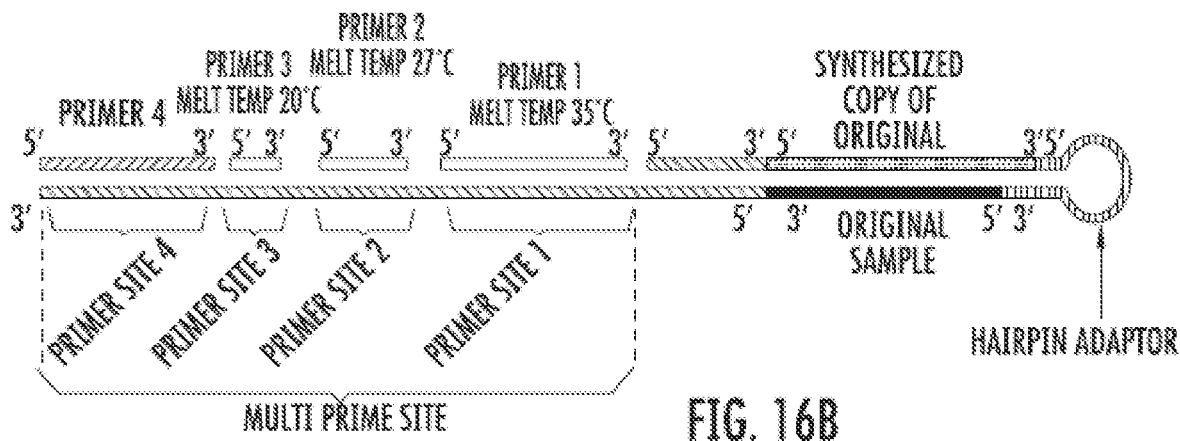
Figure 16C:
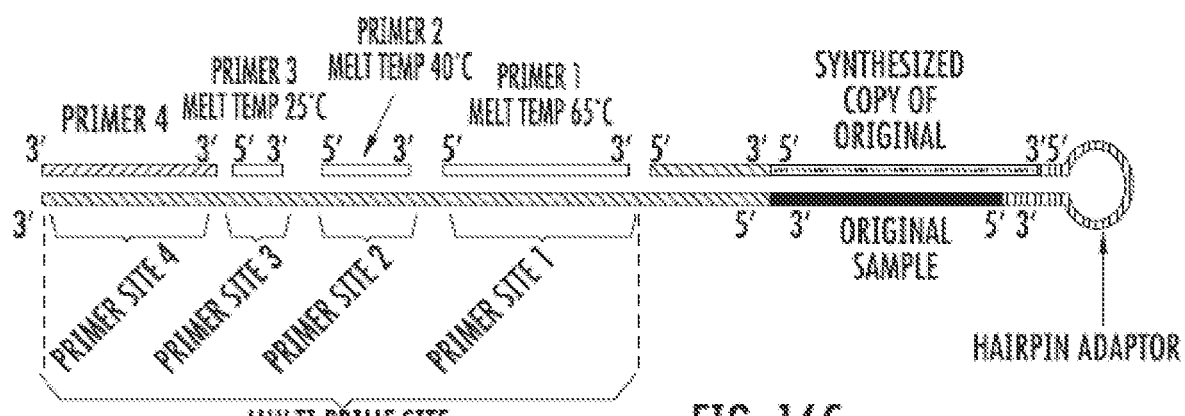

FIG. 16A-I depict a replication strategy for re-using a single primer site from a multi-primer adaptor site. FIG. 16A depicts a fully formed adaptor ligated nucleic acid molecule (from a sample), including the Original Sample, Synthesized copy of the Original Sample, a hairpin adaptor, and a multi-primer site adaptor. As exemplified in FIG. 16B, multi-primer sites with different melting temperatures are separated by small melting temperature differences. The strategy allows for the precise and deliberate reduction of temperature from a higher temperature (e.g., 35° C.) to a lower temperature (e.g., 20° C.) in steps or a linear fashion thereby permitting a predetermined primer binding sequence. In one embodiment, the methods comprises binding the primer with the highest melting temperature first, followed by binding the primer with the second highest melting temperature, and so on. Those of ordinary skill in the art will appreciate that suitable enzymes which extend new nucleic acid strands in extension reactions (e.g., open-fold replication) and suitable ligases that connect nucleic acid fragments over a wide temperature range are intended to be used. FIG. 16C exemplifies a strategy of using a multi-primer adaptor with larger differences in primer site melting temperature.

Figure 16D:
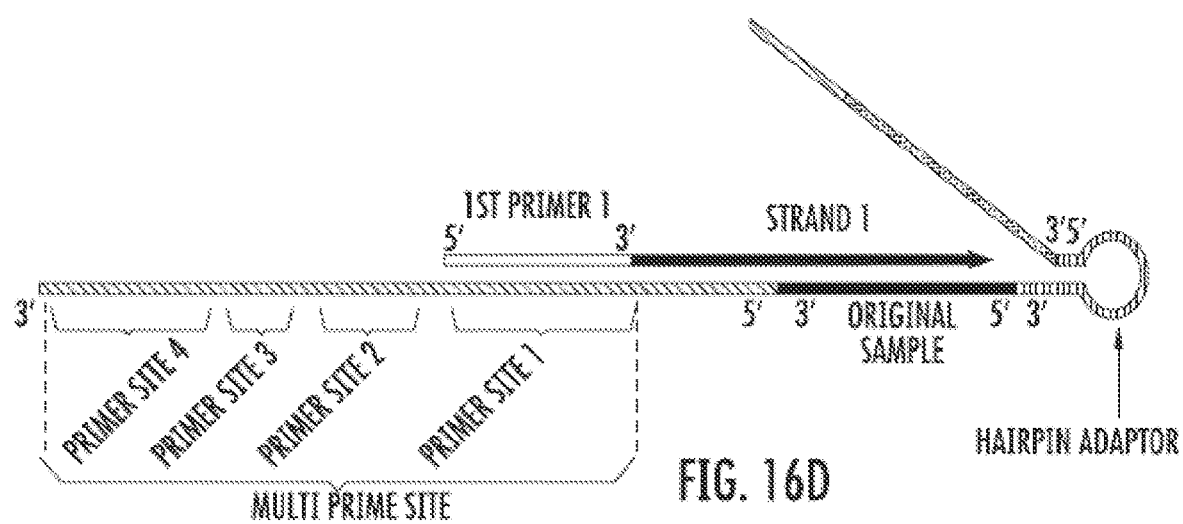
Figure 16E:
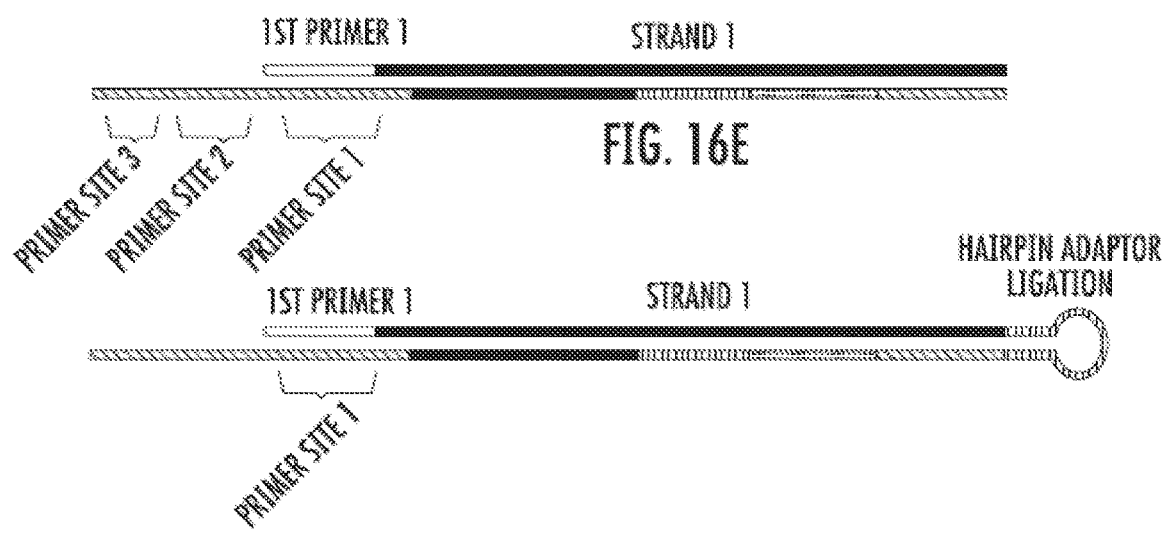

FIG. 16D exemplifies the use of a first population of a first primer ($1^{st}$ Primer 1) for extension (e.g., open-fold replication) with a first primer site (Primer Site 1). FIG. 16E depicts the first product of the extension, which includes (i) an original template strand containing the Original Sample, a Synthesized copy of the Original Sample, and (ii) a new strand containing a copy of the original template strand (Strand 1). FIG. 16E further depicts the first primer that is now part of the new strand ($1^{st}$ Primer 1) and a newly ligated hairpin adaptor (e.g., to the blunt end or single nucleotide tailed end of the extended product).

Figure 16F:
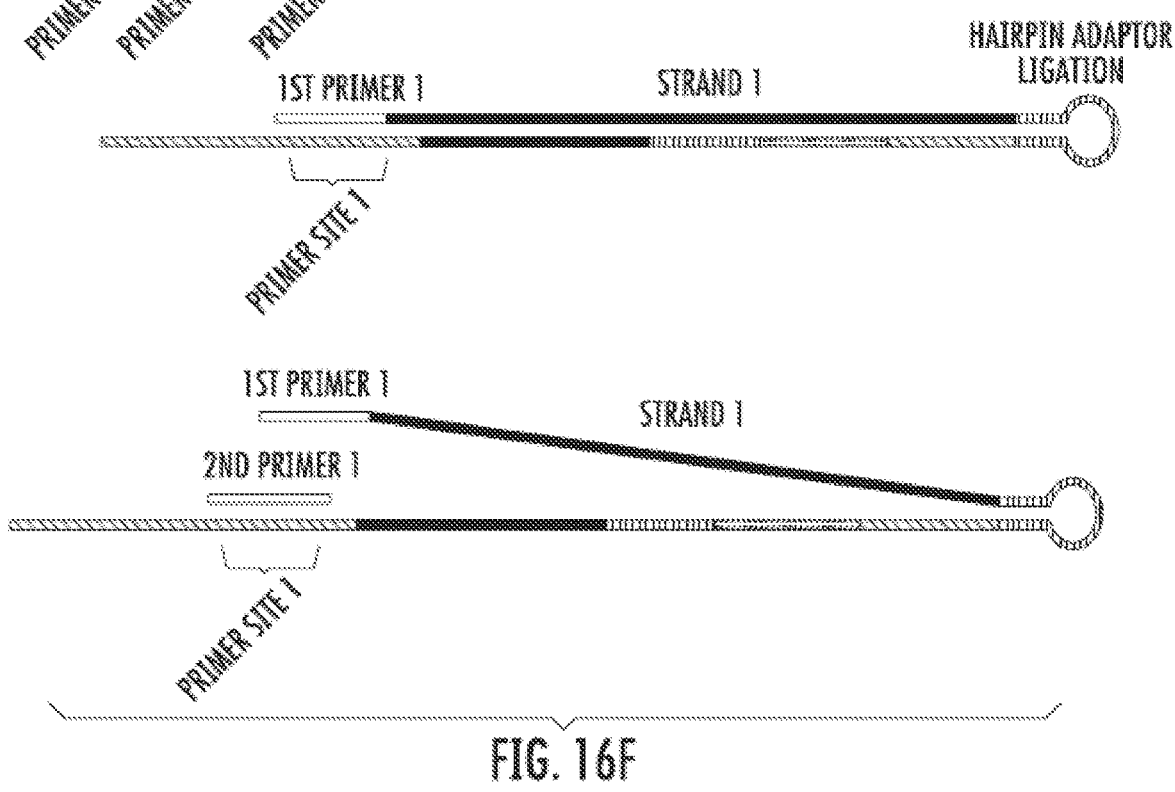

FIG. 16F shows the subsequent use of a second population of a first primer ($2^{nd}$ Primer 1) for extension (e.g., open-fold replication) with a first primer site (Primer Site 1), which competes with the first primer sequence that is part of the new strand from FIG. 16E. As discussed herein, following the extension and ligation shown in FIG. 16E, the temperature is increased to denature the double stranded duplex extension product thereby making the first primer site (Primer Site 1) available for re-hybridization of the first primer. The second population of the first primer is provided in an excess relative to the amount of extension product in order to allow the excess first primer to outcompete the pre-existing first primer sequence that is part of the extension product for hybridization to the first primer site. To help facilitate the outcompetition of the excess first primer, the temperature is rapidly cooled from the denaturing temperate to a hybridization (or re-annealing) temperature. As a result, the excess first primer re-primes to the single stranded nucleic acid and extension can be performed (e.g., open fold replication) at the same first primer site.

Figure 16G:
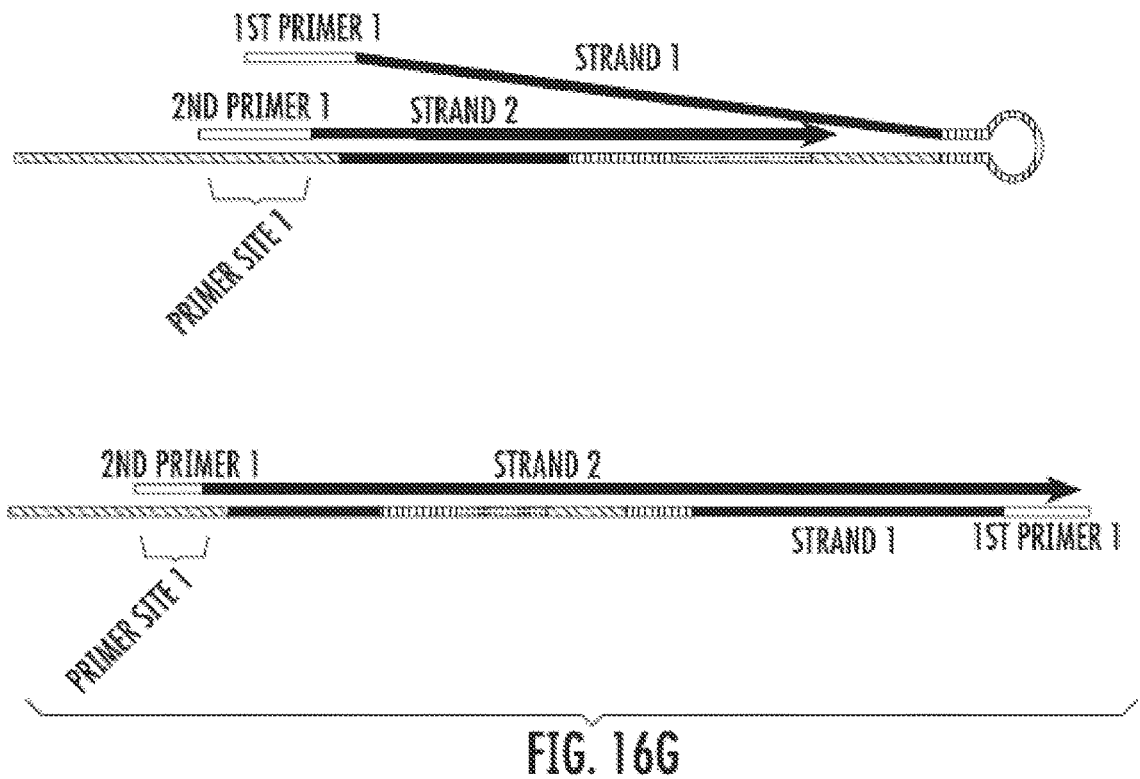

FIG. 16G exemplifies this extension using the excess first primer where Strand 2 is the newly synthesized strand. FIG. 16G also shows the fully extended strand using the excess first primer (Strand 2).

Figure 16H:
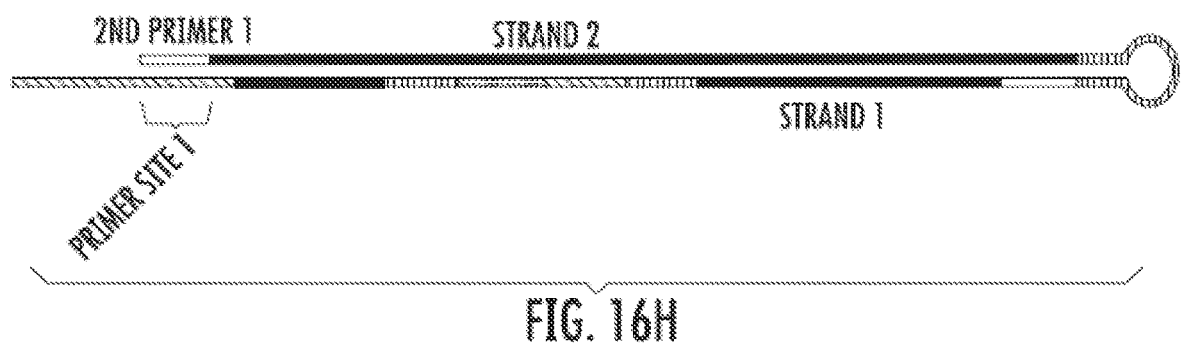

FIG. 16H exemplifies the ligation of another hairpin adaptor at the newly created end of the product of open fold replication from FIG. 16G.

Figure 16I:
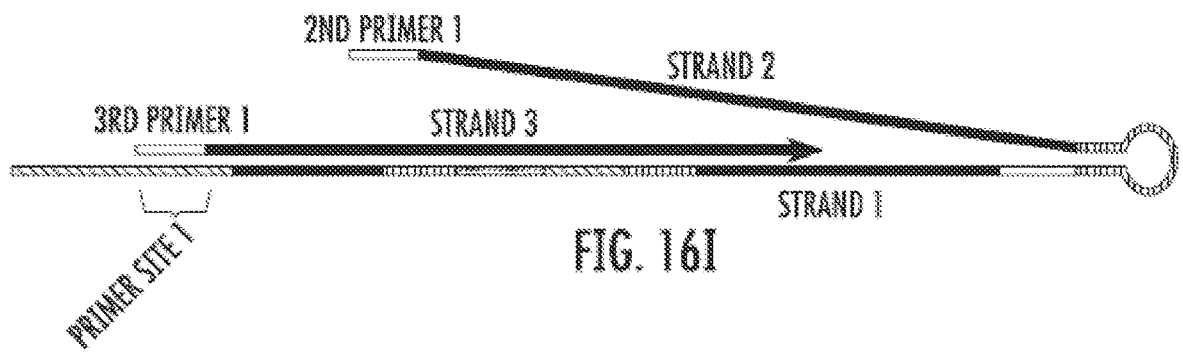

FIG. 16I exemplifies a second re-use of the first primer ($3^{rd}$ Primer 1) wherein the process is repeated with a third population the first primer and the first primer site ($3^{rd}$ Primer 1). This strategy is advantageous because it does not require as many new primer sites and the number of extensions or open fold replication cycles is limited only by the length of the sample DNA product that the user wishes to attain. It is also understood that the hairpin primer that is illustrated in FIG. 16 can be replaced at any time by a separate, different double stranded sample DNA closed at one end with a hairpin adaptor and presenting either a blunt end or 3' T tail overhang appropriate to ligate to the end of the newly created product of the open fold replication step.

IV. Open-Fold Replication—Improved Accuracy and Modified Base Calling

In one aspect, the present invention covers a method of creating single nucleic acid templates that contain the original sample fragment and at least one copy of that same fragment, which allows for a comparison of extension times for modified base positions on the original sample strand (such as methyl C) with non-modified bases in the copied portion (sequences) of the new sample strand. In one embodiment, the copy(ies) has been translated in an environment of known standard dNTPs. In another embodiment the copy(ies) have been translated in an environment of modified dNTPs that each give different nucleotide incorporation times during sequencing by synthesis. The resulting added dimension of detection signal (voltage level and nucleotide incorporation time) can be useful in determining true base to base differences in a sequence, including whether an original (non-copied) portion of the sample DNA is a modified base. In another embodiment, the template DNA comprises two representations of the original sample fragment. In one other embodiment, the two representations comprise the original (Original Sample Sense Strand) with any modified bases present and a second exact duplicate (Sense Strand Copy) containing standard nucleotides. The presence of both representations on a single larger template allows for each to (i) be read in the same sequentially presented nucleotide stream, (ii) be processed in the same nanopore, and (iii) be processed by the same polymerase. These common elements allow for a more direct comparison of the signals generated at individual base positions. For example, the extension times of modified base positions (e.g., methyl C) on the original strand can be compared to the extension times of the corresponding non-modified base positions (due to the use of standard dNTPs during the extension reaction) on the copied fragments. As a result, this should allow improved detection of modified bases whether by differences in dwell time between original (e.g., potentially modified) bases and "clean copy" bases (e.g., made from standard nucleotides), or other signal attributes of the sequencing system. In another embodiment, the translation history of the new "clean copy" from the original can be traced by studying the Antisense $1^{st}$ gen copy versus the original to remove any replication bias from the analysis. Bias induced by enzymatic replication can be error checked as the original sample strand is included at the start of the template and subsequent copies are sequentially added allowing a history of the replicates to be determined. Another advantage of this method is that base variations may be determined without chemical pretreatment.

In another aspect, the single nucleic acid templates for use in methods of modified base calling are prepared according to the methods described herein. In one embodiment, the method of preparation comprises adding asymmetrical ends to sample nucleic acid to create a circular template. In another embodiment, different adaptors are used to add the asymmetrical ends. For instance, a unidirectional extension reaction may be performed as described herein using tailing and an extension primer containing a random or universal base region (or alternatively a known nucleic acid sequence region that is complementary to a 3' region of a nucleic acid population, e.g., an amplicon population) at one end, while the other end of the extension primer comprises a unique nucleic acid sequence (see FIGS. 3A-C and 4A-D), thereby preparing the extended fragment for ligation to adaptors. In one embodiment, the method comprises ligating a first double stranded adaptor to the extended fragment at the site of the single A 3' overhang. In another embodiment, the first adaptor is a double stranded (ds) nucleic acid molecule comprising a first strand having a primer binding region containing one or more primer sites (e.g., a multi-priming site region) at one end and a first complementary nucleic acid region for binding to the second strand at the other end, wherein the first complementary region further comprises an overhang. In a preferred embodiment, the overhang comprises (i) a single T 5' overhang for ligation to a corresponding single A 3' overhang, or (ii) a second complementary nucleic acid 5' overhang sequence for hybridization to a predetermined unique sequence that is created as part of a unidirectional extension reaction as described herein. In an additional embodiment, the first adaptor further comprises a second strand that comprises a nucleic acid sequence that is complementary to the first complementary nucleic acid region of the first strand.

In another embodiment, the method further comprises ligating a second adaptor to the extended fragment at the end opposite the first adaptor. In a preferred embodiment, the second adaptor comprises a single stranded nucleic acid having an overhang and a hairpin region. In one embodiment, the overhang comprises (i) a single T 5' overhang for ligation to a corresponding single A 3' overhang, or (ii) a second complementary nucleic acid 5' overhang sequence for hybridization to a predetermined unique sequence that is created as part of a unidirectional extension reaction as described herein (e.g., see FIGS. 3-4).

Figure 9A:
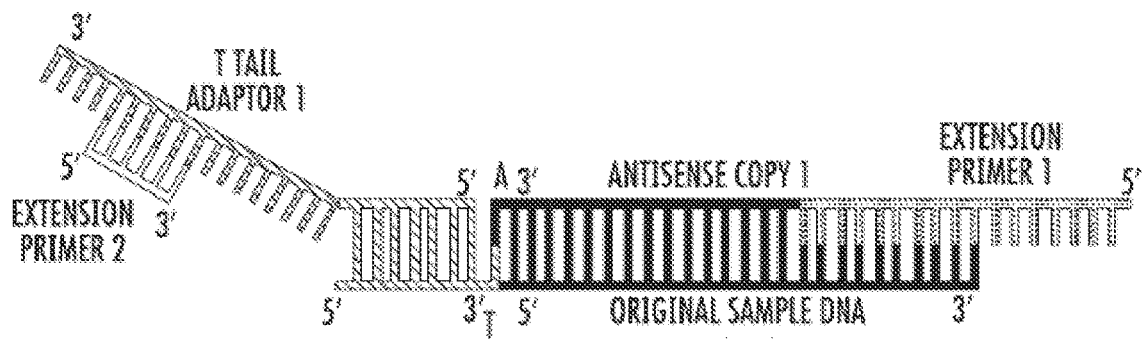
FIGS. 9A, 9B, 9C and 9D depict a strategy for a method to replicate the original sample sense and antisense strands and create an exact copy of the original sense strand for improved modified base calling.
Figure 9B:
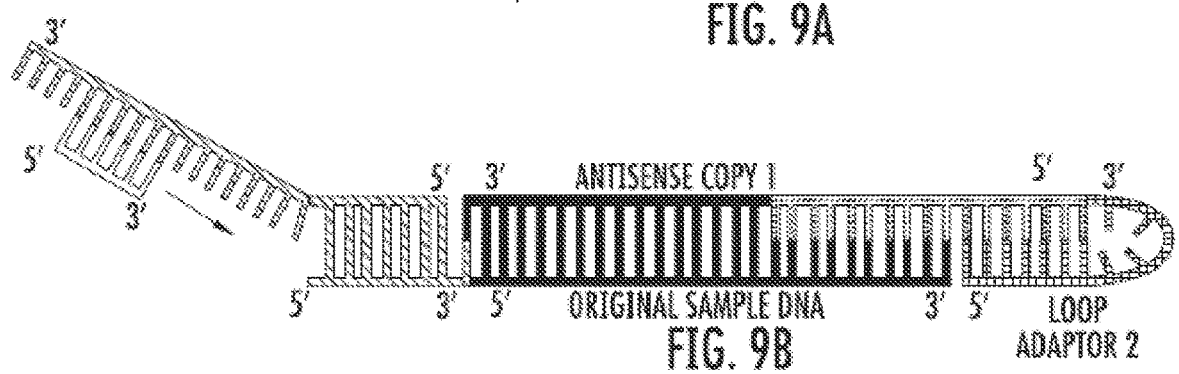
Figure 9C:
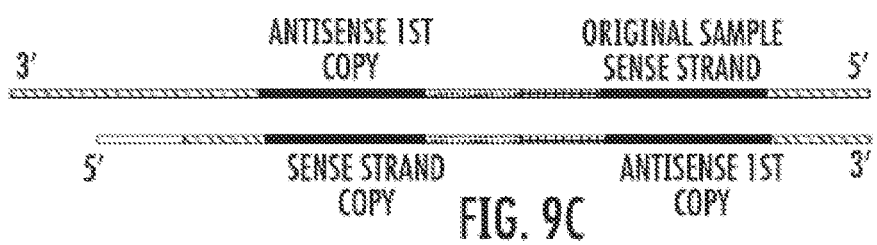
Figure 9D:
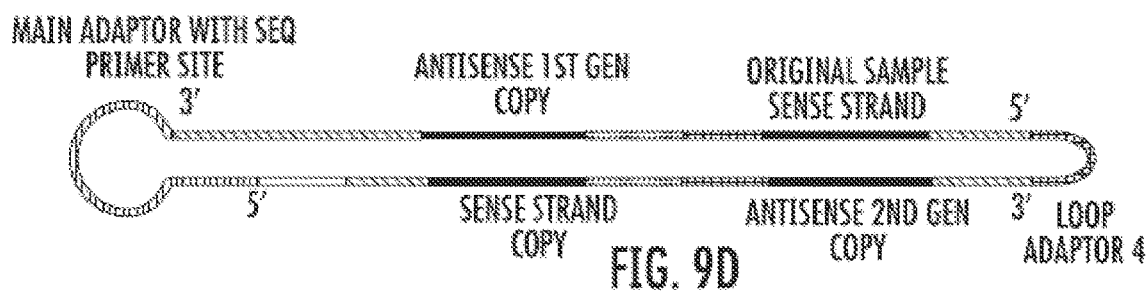

FIGS. 9A-D depict a method by which a template DNA for sequencing is created that comprises an original single strand of DNA and a copy of the original strand. FIG. 9A-C are also depicted in FIG. 4A-D. FIG. 9D shows the step of adding a Main Adaptor with a sequencing primer site (FIG. 9D, left side) and a loop adaptor 4 (FIG. 9D, right side). As in FIG. 4, FIG. 9D depicts a resulting molecule which contains three copies of the original single stranded sample.

Alternatively, where the sequence of the template nucleic acid is known (e.g., amplified nucleic acid or amplicons), a single stranded primed hairpin molecule is used to specifically prime and extend, as well as seal the 3' end of the single stranded nucleic acid using a ligase step (e.g., FIG. 2A-B. For instance, the single stranded 5' overhang Extension Primer 1 in FIG. 9A could be replaced with the hairpin molecule such that priming and sealing are provided in one step.

Expandomer-Like Moieties

Figure 18A:
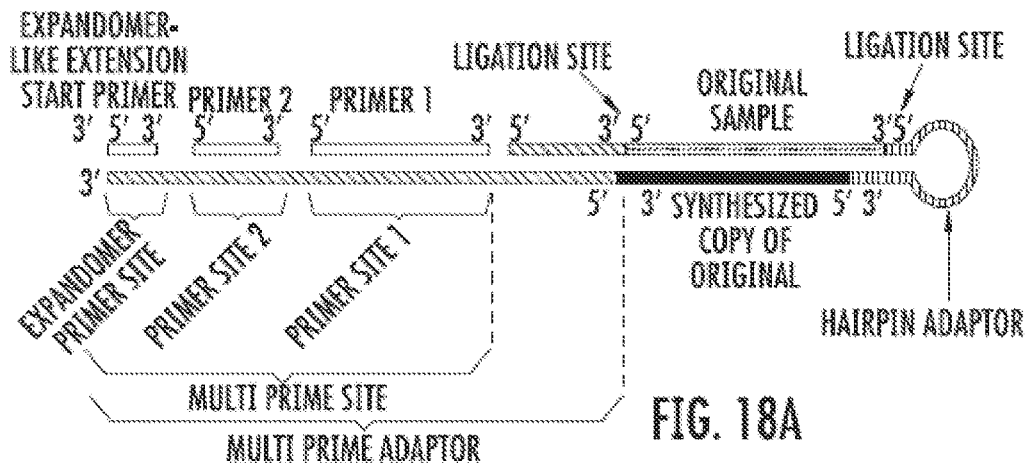
FIGS. 18A-18D depict the use of multi-primer adaptor site, which comprises an expandomer-like extension start primer site (FIGS. 18A-18C), and the optional use of a primer with a lower binding temperature (FIG. 18D).
Figure 18B:
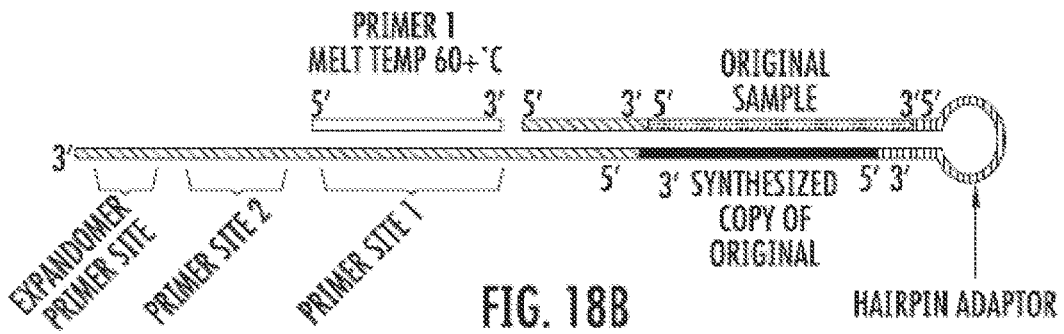
Figure 18C:
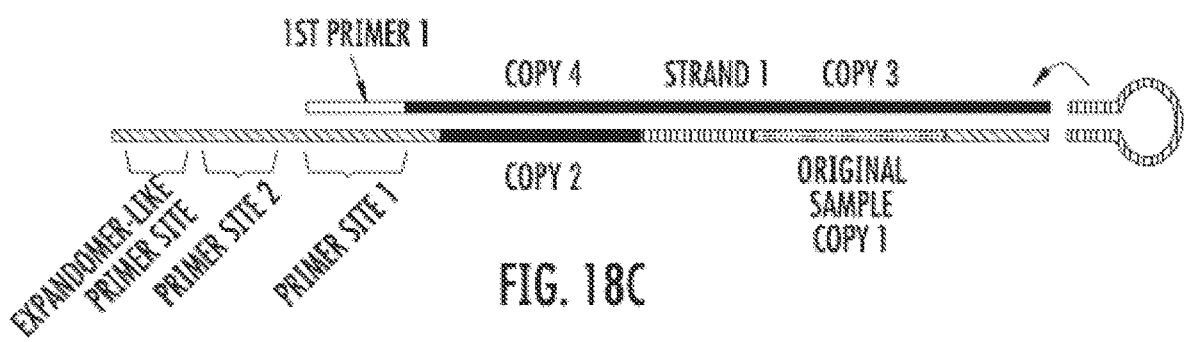
Figure 18D:
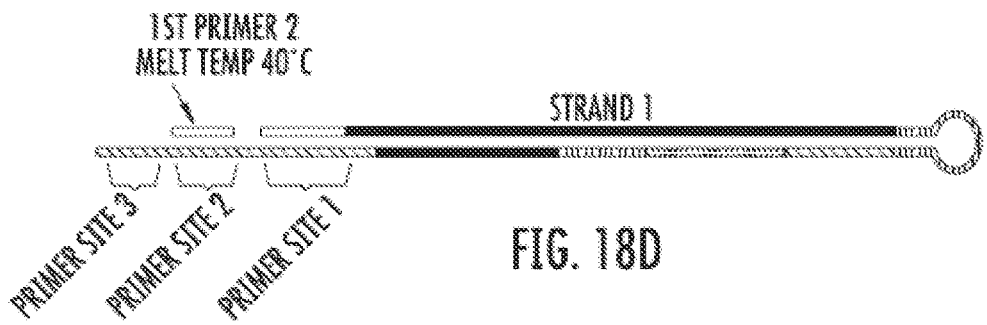

In one additional aspect, the present invention provides methods of open-fold replication that comprise the use of expandomer-like moieties. In one embodiment, a multi-primer adaptor site, as described herein, comprises an expandomer-like primer site (FIG. 18A). In one embodiment, the open fold replication may be single or multiple open fold replication cycles. FIG. 18B depicts the hybridization of Primer 1 to the Primer 1 binding site. FIG. 18C depicts the completion of the extension (i.e., after open-fold replication) resulting in copy 3 and copy 4 of the sample. The hairpin loop can be ligated to the completed double stranded molecule (as shown on the right site of the molecule). FIG. 18D depicts an optional Primer 2 hybridization, where Primer 2 has a lower binding temperature than Primer 1 allowing both primers to be in solution at the same time and selectively bind primers by lowering temperature at the appropriate time.

Figure 19:
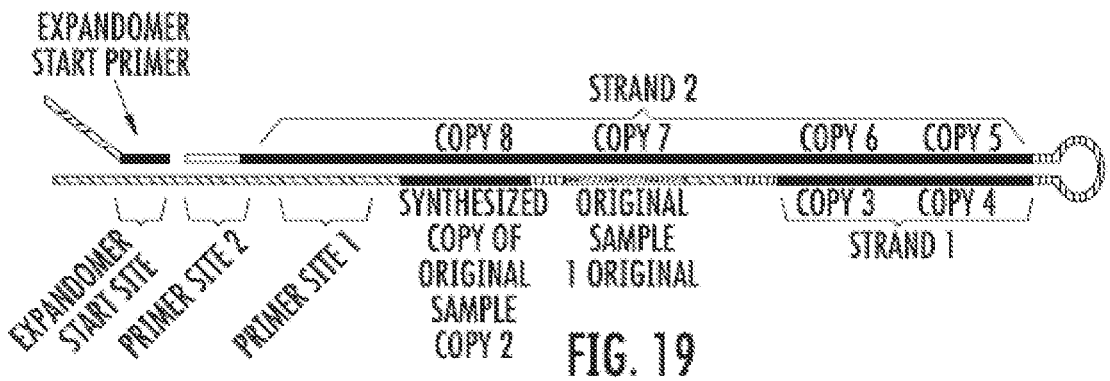
FIG. 19 depicts the use of an expandomer-like primer as part of the multi-primer adaptor site (continuation of the use depicted in FIG. 18A-18D).

FIG. 19 depicts the addition of an expandomer-like start primer (arrow) with the option of having a 5' adaptor to bind a strand to a bilayer membrane (left of the arrow). In one embodiment, the addition may be immediately before the addition of Primer 1 or 2, in which case 2 copies of the sample sequence of interest are created in an expandomer-like representation. In another embodiment, the expandomer-like primer is added after a Primer 1 extension and ligation of a circular adaptor (shown on the right side of the molecule in FIG. 19), in which case 4 copies of the sample sequence of interest are created in an expandomer-like representation. FIG. 19 depicts a Primer 2 extension as complete and a new looped adaptor ligated to the newly replicated duplex (see right side of molecule). Optionally, the primer serving as an expandomer-like starting point for strand duplication and extension may now be hybridized to appropriate hybridization site. FIG. 19 further depicts 8 copies of the original sample after 2 open-fold replication cycles from Primer Sites 1 and 2, and ligation of a third looped adaptor.

Figure 20:
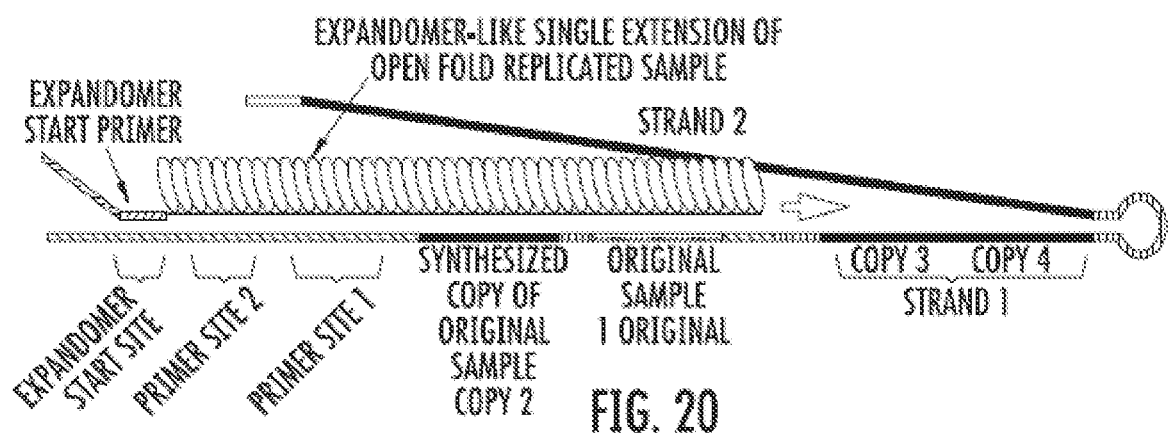
FIG. 20 depicts the use of an expandomer-like primer in open-fold replication.

FIG. 20 depicts an example of an expandomer-like start primer extension using unique expandomer-like nucleotides (e.g., nucleotides that are more readily detected in a nanopore than naturally-occurring nucleotides).

Figure 21A:
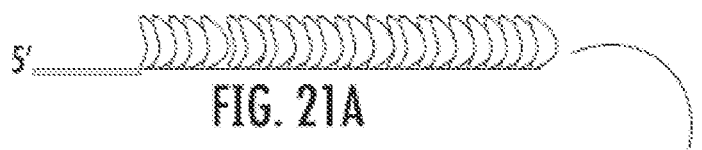
FIGS. 21A and 21B depict the release of an expandomer strand from the original template.
Figure 21B:

FIG. 21A-B depicts an example of an expandomer strand released from the original template. FIG. 21A shows the released expandomer strand and FIG. 21B shows individual reporter loops broken (e.g., chemical cleavage) resulting in a serial string of reporter sites. The linear polymer encoded with reporter moieties for each base in the original template may be pulled through a nanopore where each reporter can be read in sequence.

What is claimed is:
1. A method of preparing an asymmetric nucleic acid template for sequencing, the method comprising:
    (a) contacting a single-stranded sample nucleic acid with a first adaptor molecule, wherein the first adaptor molecule comprises: (i) a single-stranded extendible primer region, (ii) a double-stranded duplex region, and (iii) a hairpin region;
    (b) ligating the first adaptor molecule to a first end of the single-stranded sample nucleic acid;
    (c) extending the single-stranded extendible primer region of the first adaptor molecule to generate an extended nucleic acid, wherein the extended nucleic acid comprises a single A 3' overhang, and wherein the extended nucleic acid is a first complement to the single-stranded sample nucleic acid; and
    (d) ligating a second adaptor molecule to an end of the extended nucleic acid at a second end of the single-stranded sample nucleic acid, and
    wherein the first adaptor molecule and the second adaptor molecule are not identical.
2. The method of claim 1, wherein the second adaptor molecule comprises: (i) a double-stranded duplex region having an overhang region comprising a single T 3' overhang, and (ii) a hairpin region.

3. The method of claim 2, wherein the single-stranded extendible primer region of the first adaptor molecule comprises at least one universal base.

4. The method of claim 2, wherein the single-stranded extendible primer region of the first adaptor molecule comprises a region complementary to a sequence in the single-stranded sample nucleic acid.

5. The method of claim 2, wherein the second adaptor molecule comprises a primer-binding site.

6. The method of claim 2, wherein the second adaptor molecule comprises a sequencing primer site.

7. The method of claim 1, wherein the second adaptor molecule comprises a double-stranded duplex region having: (i) a first overhang region comprising a single T 3' overhang, and (ii) a second overhang region comprising a primer site region.

8. The method of claim 7, wherein the single-stranded extendible primer region of the first adaptor molecule comprises at least one universal base.

9. The method of claim 7, wherein the single-stranded extendible primer region of the first adaptor molecule comprises a region complementary to a sequence in the single-stranded sample nucleic acid.

10. The method of claim 7, wherein the second adaptor molecule comprises a primer-binding site.

11. The method of claim 7, wherein the second adaptor molecule comprises a sequencing primer site.

* * * * *